(12) United States Patent
Tepe et al.

(10) Patent No.: US 6,878,735 B2
(45) Date of Patent: *Apr. 12, 2005

(54) MULTI-SUBSTITUTED IMIDAZOLINES AND METHOD OF USE THEREOF

(75) Inventors: Jetze J. Tepe, East Lansing, MI (US); Satyamaheshwar Peddibhotla, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 12 days.

This patent is subject to a terminal disclaimer.

(21) Appl. No.: 10/347,323

(22) Filed: Jan. 17, 2003

(65) Prior Publication Data

US 2003/0232870 A1 Dec. 18, 2003

Related U.S. Application Data

(60) Provisional application No. 60/385,162, filed on May 31, 2002.

(51) Int. Cl.[7] .................. A61K 31/4164; C07D 233/26
(52) U.S. Cl. .................. 514/401; 514/402; 548/312.1; 548/334.5; 548/333.5; 548/350.1
(58) Field of Search .......................... 548/312.1, 334.5, 548/333.5, 350.1; 514/401, 402

(56) References Cited

U.S. PATENT DOCUMENTS

| | | |
|---|---|---|
| 5,804,374 A | 9/1998 | Baltimore |
| 5,821,072 A | 10/1998 | Schwartz et al. |
| 6,001,563 A | 12/1999 | Deely et al. |
| 6,318,978 B1 | 11/2001 | Burns |
| 6,410,516 B1 | 6/2002 | Baltimore |

OTHER PUBLICATIONS

Yamamoto, Y., et al., J. Clin Invest 107 135–142 (2001).
Hart, L.A., et al., Am J Respir Crit Care Med 158 1585–1592 (1998).
Coward, W.R., et al., Clin Exp Allergy 28 Suppl 3, 42–46 (1998).
Badger, A.M., et al., J. Pharmacol Exp Ther 290 587–593 (1999).
Breton, J.J., et al., J Pharmacol Exp Ther 282 459–466 (1997).
Roshak, A., et al., J Pharmacol Exp Ther 283 955–951 (1997).
Kopp, E., et al., Science 265 956–959 (1994).
Ichiyama, T., et al., Brain Res 911 56–61 (2001.
Natarajan, K., et al., Proc Natl Acad Sci USA 93 9090–9095 (1996).
M.P.Boland, Biochemical Society Transactions, vol. 29 part 6, p 674–678 (2001).
Bohrer, H., J. Clin. Invest., 972–985 (1997).
Cusack, J.C., et al., Cancer REs 60 2323–2330 (2000).
Brandes, L.M., et al., Mol Pharmacol, 60, 559–567 (2001).
Arlt, A., et al., Oncogene 20 859–858 (2001).
Cusack, J.C., et al., Cancer Res 61 3535–3540 (2001).
Hershenson, F.M.P., Synthesis, 999–1001 (1988).
Consonni, R.C., et al., J. Chem. Res (S) 188–189 (1991).
Bilodeau, M.T.C., J. Org. Chem. 63 2800–2801 (1998).
Puntener, K., et al., J. Org Chem. 65 8301–8306 (2000).
Hsiao, Y.H., J. Org. Chem. 62 3586–3591 (1997).
Dghaym, R.D. D., et al., Angew. Chem. Int. Ed. Engl. 40 3228–3230 (Sep. 2001).
Viso, A., et al., J. Org. Chem. 62 2316–2317 (1997).
M.Karin, Nature Immunology, 3, 221–227 (2002).
Baldwin, J. Clin. Invest., 3, 241–246 (2001), vol. 107.
Huang, T., et al., J. Biol. Chem., 275, 9501–9509 (2000).
Schunk, S., et al., Organic letters 2, 907–910 (2000).
Sain, B., et al., Heterocycles, 23, 1611–1614 (1985).
Peddibhotla, S., et al., Organic Letters 4 3533–3535 (Oct. 3, 2002).

Primary Examiner—Laura L. Stockton
(74) Attorney, Agent, or Firm—Ian C. McLeod

(57) ABSTRACT

A new class of imidazolines as 4-position acids or esters with very potent anti-inflammatory as well as antimicrobial activity is described. The synthesis of these imidazolines includes a multicomponent reaction applicable to a combinatorial synthetic approach. The combination of these two key characteristics provides an effective therapeutic drug in the treatment of septic shock as well as many other inflammatory (arthritis and asthma) and infectious disorders. The use of this novel class of non-steroidal agents as anti-inflammatory agents (for the treatment of asthma etc.), antibacterial agents and antiseptic agents is described. The compounds are also useful in the treatment of tumors (such as cancers). The imidazolines are potent inhibitors of the transcription factor NF-κB as well as potent activity against the Gram (+) bacterium *B. subtillus* and *B. cereus* with MIC values in the range of 50 μm/mL.

20 Claims, 3 Drawing Sheets

X-ray crystal structure of compound 1

MULTI-SUBSTITUTED IMIDAZOLINES AND METHOD OF USE THEREOF

CROSS REFERENCE TO RELATED APPLICATION

This application claims priority to provisional patent application Ser. No. 60/385,162, filed May 31, 2002.

BACKGROUND OF THE INVENTION (1) Field of the Invention

The present invention relates to novel multi-substituted 4-acid or alkyl ester or amide imidazolines and to a process for their preparation. In particular the present invention relates to the multi-substituted imidazolines containing a 4-acid or an ester group which inhibit NFκB or NFκB kinase, are anti-inflammatory and/or antimicrobial and/or chemopotentiator and/or chemosensitizers of anticancer agents.

(2) Description of Related Art

Chronic airway inflammation as seen with asthma, is associated with the over expression of inflammatory proteins called cytokines. In addition, other inflammatory mediators, such as IL-1 and TNF, play a major role in joint diseases such as rheumatoid arthritis. All of these inflammatory proteins are highly regulated by the nuclear transcription factor kappa B (NF-κB) (Yamamoto, Y., et al., J. Clin Invest 107 135–142 (2001); and Hart, L. A., et al., Am J Respir Crit Care Med 158 1585–1592 (1998)). Inhibition of this regulatory protein or its kinase by anti-inflammatory drugs has been shown to be effective in the treatment of these diseases (Yamamoto, Y., et al., J. Clin Invest 107 135–142 (2001); Coward, W. R., et al., Clin Exp Allergy 28 Suppl 3, 42–46 (1998); Badger, A. M., et al., J. Pharmacol Exp Ther 290 587–593 (1999); Breton, J. J., et al., J Pharmacol Exp Ther 282 459–466 (1997); Roshak, A., et al., J Pharmacol Exp Ther 283 955–961 (1997); Kopp, E., et al., Science 265 956–959 (1994); Ichiyama, T., et al., Brain Res 911 56–61 (2001); Hehner, S. P., et al., J Immunol 163 5617–5623 (1999); Natarajan, K., et al., Proc Natl Acad Sci USA 93 9090–9095 (1996); and Fung-Leung, W. P., et al., Transplantation 60 362–368 (1995)). The common anti-inflammatory agent, aspirin, and aspirin-like drugs, the salicylates, are widely prescribed agents to treat inflammation and their effectiveness has been attributed to NF-κB inhibition. However, in order to treat chronic inflammations, the cellular levels of these salicylates need to be at very high concentration and are generally prescribed at 1–3 miliMolar plasma concentrations (Science 265, 956–959 (1994)).

Since the discovery of penicillin, over 100 antibacterial agents have been developed to combat a wide variety of bacterial infections. Today, the clinically used antibacterial agents mainly consists of β-lactams (penicillins, carbapenems and cephalosporins), aminoglycosides, tetracyclines, sulfonamides, macrolides (erythromycin), quinolones, and the drug of last resort: vancomycin (a glycopeptide). In recent years, many new strains of bacteria have developed resistance to these drugs throughout the world. There is a need for new antimicrobials.

There is considerable interest in modulating the efficacy of currently used antiproliferative agents to increase the rates and duration of antitumor effects associated with conventional antineoplastic agents. Conventional antiproliferative agents used in the treatment of cancer are broadly grouped as chemical compounds which (1) affect the integrity of nucleic acid polymers by binding, alkylating, inducing strand breaks, intercalating between base pairs or affecting enzymes which maintain the integrity and function of DNA and RNA; and (2) chemical agents that bind to proteins to inhibit enzymatic action (e.g. antimetabolites) or the function of structural proteins necessary for cellular integrity (e.g. antitubulin agents). Other chemical compounds that have been identified to be useful in the treatment of some cancers include drugs which block steroid hormone action for the treatment of breast and prostate cancer, photochemically activated agents, radiation sensitizers and protectors.

Of special interest to this invention are those compounds that directly affect the integrity of the genetic structure of the cancer cells. Nucleic acid polymers such as DNA and RNA are prime targets for anticancer drugs. Alkylating agents such as nitrogen mustards, nitrosoureas, aziridine (such as mitomycin C) containing compounds directly attack DNA. Metal coordination compounds such as cisplatin and carboplatin similarly directly attack the nucleic acid structure resulting in lesions that are difficult for the cells to repair, which, in turn, can result in cell death. Other nucleic acid affecting compounds include anthracycline molecules such as doxorubicin, which intercalates between the nucleic acid base pairs of DNA polymers, bleomycin which causes nucleic acid strand breaks, fraudulent nucleosides such as pyrimidine and purine nucleoside analogs which are inappropriately incorporated into nucleic polymer structures and ultimately cause premature DNA chain termination. Certain enzymes that affect the integrity and functionality of the genome can also be inhibited in cancer cells by specific chemical agents and result in cancer cell death. These include enzymes that affect ribonucleotide reductase (.e.g. hydroxyurea, gemcitabine), topoisomerase I (e.g. camptothecin) and topoisomerase II (e.g. etoposide).

The topoisomerase enzymes affect the structure of supercoiled DNA, because most of the functions of DNA require untwisting. Topoisomerase I (top 1) untwists supercoiled DNA, breaking only one of the two strands, whereas topoisomerase II (top 2) breaks both.

Topoisomerase I inhibition has become important in cancer chemotherapy through the finding that camptothecin (CPT), an alkaloid of plant origin, is the best known inhibitor of top 1 and is a very potent anticancer agent. CPT is contained in a Chinese tree, *Camptotheca acuminata*. A number of analogs have become approved for commercial use to treat a number of tumor types. These include CPT-11 (irinotecan) and topotecan.

While the clinical activity of camptothecins against a number of types of cancers are demonstratable, improvements in tumor response rates, duration of response and ultimately patient survival are still sought. The invention described herein demonstrates the novel use which can potentiate the antitumor effects of chemotherapeutic drugs, including topoisomerase I inhibitors, in particular, camptothecins.

Relevant Literature

Cancer Chemotherapeutic Agents, W. O. Foye, ed., (ACS, Washington, D.C.) (1995)); Cancer Chemotherapy Handbook, R. T. Dorr and D. D. VonHoff, (Appleton and Lange, Norwalk, Conn.) (1994); and M. P. Boland, Biochemical Society Transactions (2001) volume 29, part 6, p 674–678. DNA damage signaling and NF-κB: implications for survival and death in mammalian cells.

Invasive infection with Gram positive or Gram negative bacteria often results in septic shock and death. Invasion of the blood stream by both types of bacteria (Gram positive and Gram negative) causes sepsis syndrome in humans as a result of an endotoxin, Lipopolysaccharide (LPS) (H.

Bohrer, J. Clin. Invest. 972–985 (1997)), that triggers a massive inflammation response in the host. The mechanism by which LPS caused septic shock is through the activation of the transcription factor NF-κB. Activation of this protein by its kinase initiates the massive release of cytokines resulting in a potentially fatal septic shock. For example, the pneumococcus bacteria is the leading cause of death with a mortality rate of 40% in otherwise healthy elderly individuals and staphylococcal infections are the major cause of bacteremia in US hospitals today. Septic shock, caused by an exaggerated host response to these endotoxins often leads to multiple organ dysfunction, multiple organ failure, and remains the leading cause of death in trauma patients.

NF-κB has been indicated to inhibit apoptosis (programmed cell death). Many clinically used chemotherapeutic agents (including the vinca alkaloids, vincristine and vinblastinc, camptothecin and many others) have recently been shown to activate NF-κB resulting in a retardation of their cytotoxicity. This form of resistance is commonly referred to as NF-κB mediated chemoresistance. Inhibition of NF-κB has shown to increase the sensitivity to chemotherapeutic agents of tumor cells and solid tumors.

References

Cusack, J. C.; Liu, F.; Baldwin, A. S. NF-kappa B and chemoresistance: potentiation of cancer drugs via inhibition of NF-kappa B. *Drug Resist Updat* 1999, 2, 271–273, Mayo, M. W.; Baldwin, A. S. The transcription factor NF-kaapaB: control of oncogenesis and cancer therapy resistance, Biochim Biophys Acta 2000, 1470, M55-62. Wang, C. Y.; Mayo, M. W.; Baldwin, A. S., Jr. TNF- and cancer therapy-induced apoptosis; potentiation by inhibition of NF-kappaB. Science 1996, 274, 784–787. (Cusack, J. C., Jr.; Liu, R.; Baldwin, A. S., Jr. Inducible chemoresistance to 7-ethyl-10-[4-(1-piperidino)-1-piperidino]-carbonyloxycamptothecin (CPT-11) in colorectal cancer cells and a xenograft model is overcome by inhibition of nuclear factor-kaapaB activation. *Cancer Res* 2000, 60, 2323–2330. Brandes, L. M.; Lin, Z. P.; Patierno, S. R.; Kennedy, K. A. Reversal of physiological stress-induced resistance to topoisomerase II inhibitors using an inducible phosphorylation site-deficient mutant of 1 kappa B alpha. *Mol Pharmacol* 2001, 60, 559–567, Arlt, A.; Vorndamm, J.; Breitenbroich, M.; Folsch, U. R.; Kalthoff, H. et al. Inhibition of NF-kappaB sensitizes human pancreatic carcinoma cells to apoptosis induced by etoposide (VP16) or doxorubicin. *Oncogene* 2001, 20, 859–868. Cusack, J. C., Jr.; Liu, R.; Houston, M.; Abendroth, K.; Elliott, P. J. et al. Enhanced chemosensitivity to CPT-11 with proteasome inhibitor PS-341; implications for systemic nuclear factor kappaB inhibition.

*Cancer Res* 2001 61, 3535–3540.

1,3 Dipolar cycloadditions reactions utilizing azlactones of "munchones" provide a general route for the synthesis of pyrroles and imidazoles (Hershenson, F. M. P., Synthesis 999–1001 (1988); Consonni, R. C., et al., J. chem. Research (S) 188–189 (1991); and Bilodeau, M. T. C., J. Org. Chem. 63 2800–2801 (1998)). This approach has not yet been reported for the imidazoline class of heterocycles. The synthetic and pharmacological interest in efficient syntheses of imidazolines has fueled the development of several diverse synthetic approaches (Puntener, K., et al., J. Org Chem 65 8301–8306 (2000); Hsiao, Y. H., J. Org. Chem. 62 3586–3591 (1997)). Recently, Arndtsen et al reported synthesis of symmetrically substituted imidazoline-4-carboxylic acids via a Pd-catalyzed coupling of an imine, acid chloride and carbon monoxide (Dghaym, R. D. D., et al., Angew. Chem. Int. Ed. Engl. 40 3228–3230 (2001)). In addition, diastereoselective 1,3-dipolar cycloaddition of azomethine ylides has been reported from amino acid esters with enantiopure sulfinimines to yield Nsulfinyl imidazolidines (Viso, A., et al., J. Org. Chem. 62 2316–2317 (1997)).

U.S. Pat. No. 6,318,978 to Ritzeler et al describes 3,4-benzimidazoles which are structurally quite different than those of the present invention. They inhibit NFκB kinase. As can be seen, activity is retained where there are numerous different substituents in the imidazoline and benzene rings. M. Karin, Nature immunology, 3, 221–227 (2002); Baldwin, J. Clin. Invest., 3, 241–246 (2001); T. Huang et al, J. Biol. Chem., 275, 9501–9509 (2000); and J. Cusack and Baldwin, Cancer Research, 60, 2323–2330 (2000) describe the effect of activation of NFκB on cancer. U.S. Pat. Nos. 5,804,374 and 6,410,516 to Baltimore describe NFκB inhibition which are incorporated by reference.

Patents of interest for the general methodology of inhibition are set forth in U.S. Pat. No. 5,821,072 to Schwartz et al and U.S. Pat. No. 6,001,563 to Deely et al.

Objects

It is an object of the present invention to provide novel compounds which are anti-inflammatory, antimicrobial and inhibit NFκB or NFκB kinase. It is also an object of the present invention to provide for inhibition of cancers by inhibition of chemoresistance. It is further an object of the present invention to provide a novel process for the preparation of such compounds. These and other objects will become increasingly apparent by reference to the following description and the drawings.

SUMMARY OF THE INVENTION

The present invention relates to a method for inhibiting inflammation in a mammal which comprises administering a multi-substituted 4-acid or 4-alkyl ester imidazoline to the mammal in an amount sufficient to inhibit the inflammation.

The present invention also relates to a method of inhibiting the activation of the NF-κB protein by inhibition of the degradation of the inhibitory protein, I kappa B, or its kinases and the ability to inhibit NF-κB which comprises of contacting the protein or its activating proteins with a multi-substituted 4-acid or 4-alkyl ester or amide imidazoline in an amount sufficient to inhibit activation of the protein.

The present invention further relates to a method of inhibiting a cancer which comprises contacting the cancer with a multi-substituted imidazoline in an amount sufficient to inhibit the cancer.

The present invention relates to an imidazoline of the formula:

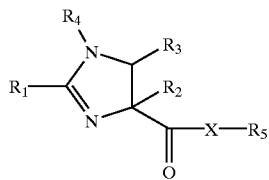

wherein $R_1$, $R_2$, $R_3$ and $R_4$ are selected from the group consisting of alkyl, acyl, aryl, arylalkyl, heteroaryl containing 5 to 14 ring members, and heterocyclic containing 5 to 12 ring members; X is selected from the group consisting of O and S; and $R_5$ is selected from the group consisting of hydrogen, alkyl, acyl, aryl arylalkyl, heteroaryl, $NH_2$, NH—$R_6$ and

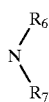

where $R_6$ and $R_7$ are selected from the group consisting of hydrogen, alkyl, aryl, arylalkyl, and heteroaryl and heterocyclic, which may be the same or different.

Further the present invention relates to an imidazoline of the formula

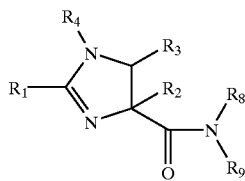

wherein $R_1$, $R_2$, $R_3$ and $R_4$ are selected from the group consisting of alkyl, acyl, aryl, arylalkyl, heteroaryl containing 5 to 14 ring members, and heterocyclic containing 5 to 12 ring members; and wherein $R_8$ and $R_9$ and selected from the group consisting of hydrogen, alkyl, aryl, arylalkyl, heteroaryl and heterocyclic, which may be the same or different.

Further, the present invention relates to a process for the preparation of an amino imidazoline which comprises reacting an imidazoline of the formula:

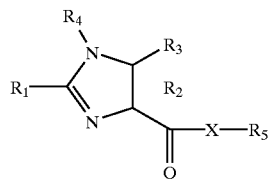

wherein $R_1$, $R_2$, $R_3$ and $R_4$ are selected from the group consisting of alkyl, acyl, aryl, arylalkyl, heteroaryl containing 5 to 14 ring members, and heterocyclic containing 5 to 12 ring members; X is selected from the group consisting of O and S; and $R_5$ is selected from the group consisting of hydrogen, alkyl, acyl, aryl arylalkyl, heteroaryl, $NH_2$, $NH-R_6$ and

where $R_6$ and $R_7$ and selected from the group consisting of hydrogen, alkyl, aryl, arylalkyl, and heteroaryl and heterocyclic, which may be the same or different, with an amine of the formula:

to produce a compound of the formula:

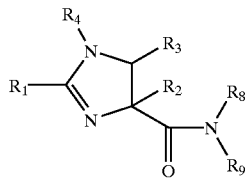

wherein $R_8$ and $R_9$ are selected from the group consisting of hydrogen, alkyl, acyl, arylalkyl and heteroalkyl, which may be the same or different.

The present invention relates to an imidazoline of the formula

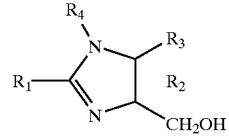

wherein $R_1$, $R_2$, $R_3$ and $R_4$ are selected from the group consisting of alkyl, acyl, aryl, aralkyl, heteroaryl containing 5 to 14 ring members, and heterocyclic containing 5 to 12 ring members; and $R_5$ is selected from the group consisting of hydrogen and an alkyl group, all of which are optionally substituted.

The present invention particularly relates to an imidazoline of the formula:

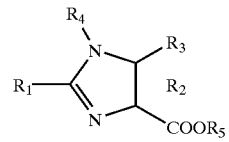

wherein $R_1$, $R_2$, $R_3$ and $R_4$ are each individually selected from the group consisting of alkyl, acyl, aryl, arylalkyl, heteroaryl containing 5 to 14 ring members, and heterocyclic containing 5 to 12 ring members; and $R_5$ is selected from the group consisting of hydrogen and an alkyl group, all of which are optionally substituted. Preferably $R_1$ is phenyl; $R_4$ is benzyl; $R_5$ is lower alkyl containing 1 to 4 carbon atoms. Also preferably $R_5$ is ethyl; $R_2$ is lower alkyl containing 1 to 4 carbon atoms. Most preferably $R_2$ is methyl and $R_3$ is selected from the group consisting of phenyl and substituted phenyl.

The imidazoline(Compound 1) wherein $R_1$ is phenyl, $R_2$ is methyl, $R_3$ is phenyl, $R_4$ is benzyl and $R_5$ is H is a preferred compound. The imidazoline (Compound 2) wherein $R_1$ is phenyl, $R_2$ is methyl, $R_3$ is 4-methoxyphenyl, $R_4$ is benzyl and $R_5$ is H is a preferred compound. The imidazoline (Compound 3) wherein $R_1$ is phenyl, $R_2$ is methyl, $R_3$ is phenyl, $R_4$ is 4-fluorophenyl and $R_5$ is H is a preferred compound. The imidazoline (compound 4) wherein $R_1$ is phenyl, $R_2$ is phenyl, $R_3$ is phenyl, $R_4$ is benzyl and $R_5$ is H is a preferred compound. The imidazoline (Compound 5) wherein $R_1$ is phenyl, $R_2$ is 1H-indol-3-ylmethyl, $R_3$ is phenyl, $R_4$ is benzyl and $R_5$ is H is a preferred compound. The imidazoline (Compound 6) wherein $R_1$ is phenyl, $R_2$ is methyl, $R_3$ is pyridin-4-yl, $R_4$ is benzyl and $R_5$ is H is a preferred compound. The imidazoline (Compound 7) wherein $R_1$ is phenyl, $R_2$ is methyl, $R_3$ is phenyl, $R_4$ is H and $R_5$ is H is a preferred compound. The imidazoline (Compound 8) wherein $R_1$ is phenyl, $R_2$ is methyl, $R_3$ is ethoxycarbonyl, $R_4$ is H and $R_5$ is H is a preferred compound. The imidazoline (Compound 9) wherein $R_1$ is phenyl, $R_2$ is methyl, $R_3$ is pyridin-4-yl, $R_4$ is benzyl and $R_5$ is Et is a preferred compound. The imidazoline (Compound 10) wherein $R_1$ is phenyl, $R_2$ is methyl, $R_3$ is phenyl, $R_4$ is benzyl and $R_5$ is Et is a preferred compound.

The present invention also relates to a process for the preparation of imidazoline of the formula:

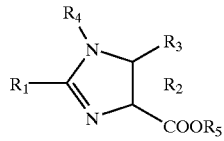

wherein $R_1$, $R_2$, $R_3$ and $R_4$ are selected from the group consisting of alkyl, acyl, aryl, aralkyl, heteroaryl containing 5 to 14 ring members, and heterocyclic containing 5 to 12 ring members; and $R_5$ is selected from the group consisting of hydrogen and an alkyl group, all of which are optionally substituted, which comprises:

(a) reacting a reaction mixture of
(1) an oxazolone of the formula:

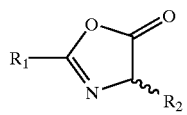

(2) a ketone of the formula:
$R_3$=O; and
(3) an amine of the formula:

in the presence of trimethyl silyl chloride or an acid chloride and a solvent for the reactants in the absence of water in the presence of a non-reactive gas and at a temperature between about 0 and 100° C. to produce the imidazoline; and (b) separating the imidazoline from the reaction mixture. The imidazoline can be esterified by reaction with an alcohol. The imidazoline is most preferably esterified by reaction with the alcohol and sulfonyl dichloride.

The present invention relates to a method for inhibiting inflammation in a mammal which comprises administering an imidazoline of the formula:

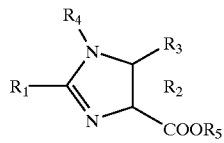

wherein $R_1$, $R_2$, $R_3$ and $R_4$ are selected from the group consisting of alkyl, acyl, aryl, aralkyl, heteroaryl containing 5 to 14 ring members, and heterocyclic containing 5 to 12 ring members; and $R_5$ is selected from the group consisting of hydrogen and an alkyl group, all of which are optionally substituted, to the mammal in an amount sufficient to inhibit the inflammation. Preferably the mammal is human. The mammal can be a lower mammal. The administration can be oral, topical, or by injection (such as intravenous) into the mammal.

The present invention also relates to a method for inhibiting a microorganism which comprises:

administering an effective amount of a compound of the formula:

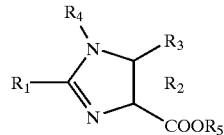

wherein $R_1$, $R_2$, $R_3$ and $R_4$ are selected from the group consisting of alkyl, acyl, aryl, aralkyl, heteroaryl containing 5 to 14 ring members, and heterocyclic containing 5 to 12 ring members; and $R_5$ is selected from the group consisting of hydrogen and an alkyl group, all of which are optionally substituted, to inhibit the microorganism. The inhibition can be in vitro or in vivo. The administration can be to a lower mammal or to a human. The administration can be oral, by injection into the mammal, or topical.

Further, the present invention relates to a method of inhibiting degradation of a protein which is NF-κB or NF-κB kinase which comprises contacting the protein with a compound of the formula:

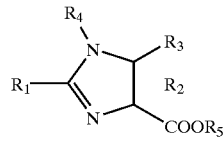

wherein $R_1$, $R_2$, $R_3$ and $R_4$ are selected from the group consisting of alkyl, acyl, aryl, aralkyl, heteroaryl containing 5 to 14 ring members, and heterocyclic containing 5 to 12 ring members; and $R_5$ is selected from the group consisting of hydrogen and an alkyl group, all of which are optionally substituted. The compounds are also useful in the treatment of tumors (cancers) where NFκB is involved. The inhibition is preferably in vivo.

$R_1$ is
(1) phenyl, mono- or disubstituted independently of one another by
  (1) (1) —CN;
  (1) (2) —NO$_2$;
  (1) (3) —O—(C$_1$–C$_4$)-alkyl;
  (1) (4) —NH$_2$; or
  (1) (5) —(C$_1$–C$_4$)-alkyl-NH$_2$;
  (1) (6) -x, wherein x is a halogen.
(2) heteroaryl having 5 to 14 ring members, in which the heteroaryl is unsubstituted or mono-, di-, or trisubstituted independently of one another by —N—R$^{14}$, in which R$^{14}$ is —(C$_1$–C$_6$)-alkyl, —(C$_3$–C$_6$)-cycloalkyl, phenyl, halogen, —OH, or —(C$_1$–C$_4$)-alkyl; or
(3) a heterocycle having 5 to 12 ring members, in which the heterocycle is unsubstituted or mono-, di-, or trisubstituted independently of one another by —N—R$^{14}$, in which R$^{14}$ is —(C$_1$–C$_6$)-alkyl, —(C$_3$–C$_6$)-cycloalkyl, phenyl, halogen, —OH, or —(C$_1$–C$_4$)-alkyl.

The term "halogen" is understood as meaning fluorine, chlorine, bromine, or iodine. The term "aryl" is understood as meaning aromatic hydrocarbon groups having 6 to 14 carbon atoms in the ring. (C$_6$–C$_{14}$)-Aryl groups are, for example, phenyl, naphthyl, for example, 1-naphthyl, 2-naphthyl, biphenylyl, for example, 2-biphenylyl, 3-biphenylyl, and 4-biphenylyl, anthryl, or fluorenyl. Biphenylyl groups, naphthyl groups, and, in particular, phenyl groups are preferred aryl groups. Aryl groups, in particular phenyl groups, can be mono-substituted or polysubstituted, preferably monosubstituted, disubstituted, or trisubstituted, by identical or different groups, preferably by groups selected from ($C_1$–$C_8$)-alkyl, in particular ($C_1$–$C_4$)-alkyl, ($C_1$–$C_8$)-alkoxy, in particular ($C_1$–$C_4$)-alkoxy, halogen, nitro, amino, trifluoromethyl, hydroxyl, hydroxy-($C_1$–$C_4$)-alkyl such as hydroxymethyl, 1-hydroxyethyl, or 2-hydroxyethyl, methylenedioxy, ethylenedioxy, formyl, acetyl, cyano, hydroxycarbonyl, aminocarbonyl, ($C_1$–$C_4$)-alkoxycarbonyl, phenyl, phenoxy, benzyl, benzyloxy, or tetrazolyl. Further, when aryl is phenyl, phenyl is optionally mono- or disubstituted independently of one another by —CN, —$NO_2$, —O—($C_1$–$C_4$)-alkyl, —N($R^{11}$)$_2$, —NH—C (O)—$R^{11}$, —S(O)$_x$$R^1$, in which x is the integer 0, 1, or 2, —C(O)—$R^{11}$, in which $R^{11}$ is as defined above, or —($C_1$–$C_4$)-alkyl-$NH_2$. The same applies, for example, to groups such as arylalkyl or arylcarbonyl. Arylalkyl groups are, in particular, benzyl and also 1- and 2-naphthylmethyl, 2-, 3-, and 4-biphenylylmethyl, and 9-fluorenylmethyl. Substituted arylalkyl groups are, for example, benzyl groups and naphthylmethyl groups substituted in the aryl moiety by one or more ($C_1$–$C_8$)-alkyl groups, in particular ($C_1$–$C_4$)-alkyl groups, for example, 2-, 3-, and 4-methylbenzyl, 4-isobutylbenzyl, 4-tert-butylbenzyl, 4-octylbenzyl, 3,5-dimethylbenzyl, pentamethylbenzyl, 2-, 3-, 4-, 5-, 6-, 7-, and 8-methyl-1-naphthylmethyl, 1-, 3-, 4-, 5-, 6-, 7-, and 8-methyl-2-naphthylmethyl, by one or more ($C_1$–$C_8$)-alkoxy groups, in particular ($C_1$–$C_4$)-alkoxy groups, benzyl groups, and naphthylmethyl groups substituted in the aryl moiety for example, 4-methoxybenzyl, 4-neopentyloxybenzyl, 3,5-dimethoxybenzyl, 3,4-methylenedioxybenzyl, 2,3,4-trimethoxybenzyl, nitrobenzyl groups, for example, 2-, 3-, and 4-nitrobenzyl, halobenzyl groups, for example, 2-, 3-, and 4-chloro- and 2-, 3-, and 4-fluorobenzyl, 3,4-dichlorobenzyl, pentafluorobenzyl, trifluoromethylbenzyl groups, for example, 3- and 4-trifluoromethylbenzyl, or 3,5-bis(trifluoromethyl)benzyl.

In monosubstituted phenyl groups, the substituent can be located in the 2-position, the 3-position, or the 4-position. Disubstituted phenyl can be substituted in the 2,3-position, the 2,4-position, the 2,5-position, the 2,6-position, the 3,4-position, or the 3,5-position. In trisubstituted phenyl groups, the substituents can be located in the 2,3,4-position, the 2,3,5-position, the 2,4,5-position, the 2,4,6-position, the 2,3,6-position, or the 3,4,5-position.

The explanations for the aryl groups apply accordingly to divalent arylene groups, for example, to phenylene groups that can be present, for example, as 1,4-phenylene or as 1,3-phenylene.

Phenylene-($C_1$–$C_6$)-alkyl is in particular phenylenemethyl (—$C_6H_4$—$CH_2$—) and phenyleneethyl. ($C_1$–$C_6$). Alkylenephenyl is in particular methylenephenyl (—$CH_2$—$C_6H_4$—). Phenylene-($C_1$–$C_6$)-alkenyl is in particular phenyleneethenyl and phenylenepropenyl.

The expression "heteroaryl having 5 to 14 ring members" represents a group of a monocyclic or polycyclic aromatic system having 5 to 14 ring members, which contains 1, 2, 3, 4, or 5 heteroatoms as ring members. Examples of heteroatoms are N, O, and S. If a number of heteroatoms are contained, these can be identical or different. Heteroaryl groups can likewise be monosubstituted or polysubstituted, preferably monosubstituted, disubstituted, or trisubstituted, by identical or different groups selected from ($C_1$–$C_8$)-alkyl, in particular ($C_1$–$C_4$)-alkyl, ($C_1$–$C_8$)-alkoxy, in particular ($C_1$–$C_4$)-alkoxy, halogen, nitro, —N($R^{11}$)$_2$, trifluoromethyl, hydroxyl, hydroxy-($C_1$–$C_4$)-alkyl such as hydroxymethyl, 1-hydroxyethyl, or 2-hydroxyethyl, methylenedioxy, formyl, acetyl, cyano, hydroxycarbonyl, aminocarbonyl, ($C_1$–$C_4$)-alkoxycarbonyl, phenyl, phenoxy, benzyl, benzyloxy, or tetrazolyl. Heteroaryl having 5 to 14 ring members preferably represents a monocyclic or bicyclic aromatic group which contains 1, 2, 3, or 4, in particular 1, 2, or 3, identical or different heteroatoms selected from N, O, and S, and which can be substituted by 1, 2, 3, or 4, in particular 1, 2, or 3, identical or different substituents selected from ($C_1$–$C_6$)-alkyl, ($C_1$–$C_6$)-alkoxy, fluorine, chlorine, nitro, —N($R^{11}$)$_2$, trifluoromethyl, hydroxyl, hydroxy ($C_1$–$C_4$)-alkyl, ($C_1$–$C_4$)-alkoxycarbonyl, phenyl, phenoxy, benzyloxy, and benzyl. Heteroaryl particularly preferably represents a monocyclic or bicyclic aromatic group having 5 to 10 ring members, in particular a 5-membered or 6-membered monocyclic aromatic group which contains 1, 2, or 3, in particular 1 or 2, identical or different heteroatoms selected from N, O, and S, and can be substituted by 1 or 2 identical or different substituents selected from ($C_1$–$C_4$)-alkyl, halogen, hydroxyl, —N($R^{11}$)$_2$, ($C_1$–$C_4$)-alkoxy, phenyl, phenoxy, benzyloxy, and benzyl. $R^{11}$ is as defined in substituent $R^9$ of formula I.

The expression "heterocycle having 5 to 12 ring members" represents a monocyclic or bicyclic 5-membered to 12-membered heterocyclic ring that is partly saturated or completely saturated. Examples of heteroatoms are N, O, and S. The heterocycle is unsubstituted or substituted on one or more carbons or on one or more heteroatoms by identical or different substituents. These substituents have been defined above for the radical heteroaryl. In particular, the heterocyclic ring is monosubstituted or polysubstituted, for example, monosubstituted, disubstituted, trisubstituted, or tetrasubstituted, on carbons by identical or different groups selected from ($C_1$–$C_8$)-alkyl, for example, ($C_1$–$C_4$)-alkyl, ($C_1$–$C_8$)-alkoxy, for example, ($C_1$–$C_4$)-alkoxy such as methoxy, phenyl-($C_1$–$C_4$)-alkoxy, for example, benzyloxy, hydroxyl, oxo, halogen, nitro, amino, or trifluoromethyl, and/or it is substituted on the ring nitrogens in the heterocyclic ring by ($C_1$–$C_8$)-alkyl, for example, ($C_1$–$C_4$)-alkyl such as methyl or ethyl, by optionally substituted phenyl or phenyl-($C_1$–$C_4$)-alkyl, for example, benzyl. Nitrogen heterocycles can also be present as N-oxides or as quaternary salts.

Examples of the expressions heteroaryl having 5 to 14 ring members or heterocycle having 5 to 12 ring members are groups which are derived from pyrrole, furan, thiophene, imidazole, pyrazole, oxazole, isoxazole, thiazole, isothiazole, tetrazole, 1,3,4-oxadiazole, 1,2,3,5-oxathiadiazole-2-oxides, triazolones, oxadiazolones, isoxazolones, oxadiazolidinediones, triazoles which are substituted by F, CN, $CF_3$, or COO—($C_1$–$C_4$)-alkyl, 3-hydroxypyrrole-2,4-diones, 5-oxo-1,2,4-thiadiazoles, pyridine, pyrazine, pyrimidine, indole, isoindole, indazole, phthalazine, quinoline, isoquinoline, quinoxaline, quinazoline, cinnoline, carboline, and benzo-fused, cyclopenta-, cyclohexa-, or cyclohepta-fused derivatives of these hterocycles. Particularly preferred groups are 2- or 3-pyrrolyl, phenylpyrrolyl such as 4- or 5-phenyl-2-pyrrolyl, 2-furyl, 2-thienyl, 4-imidazolyl, methylimidazolyl, for example, 1-methyl-2,4-, or 5-imidazolyl, 1,3-thiazol-2-yl, 2-pyridyl, 3-pyridyl, 4-pyridyl, 2-, 3-, or 4-pyridyl-N-oxide, 2-pyrazinyl, 2-, 4-, or 5-pyrimidinyl, 2-, 3-, or 5-indolyl, substituted 2-indolyl, for example, 1-methyl-, 5-methyl-, 5-methoxy-, 5-benzyloxy-, 5-chloro-, or 4,5-dimethyl-2-indolyl, 1-benzyl-2- or -3-indolyl, 4,5,6,7-tetrahydro-2-indolyl, cyclohepta[b]-5-pyrrolyl, 2-, 3-, or 4-quinolyl, 1-, 3-, or 4-isoquinolyl, 1-oxo-1,2-dihydro-3-isoquinolyl, 2-quinoxalinyl, 2-benzofuranyl, 2-benzothienyl, 2-benzoxazolyl, or benzothiazolyl, or dihydropyridinyl, pyrrolidinyl, for example, 2- or 3-(N-methylpyrrolidinyl), piperazinyl, morpholinyl, thiomorpholinyl, tetrahydrothienyl, or benzodioxolanyl.

Thus methods and compositions are provided for the treatment of a host with a cellular proliferative disease, particularly a neoplasia. In the subject methods, pharmaceutically acceptable imidazolines and an antiproliferative agent are administered, preferably systemically.

Methods and compositions are provided for the treatment of a host with a cellular proliferative disease, particularly a neoplasia. In the subject methods, a pharmaceutically acceptable imidazoline is administered, preferably systemically, in conjunction with an antiproliferative agent to improve the anticancer effects. In a preferred embodiment, the imidazoline provides a chemopotentiator effect.

A chemical agent is a chemopotentiator when it enhances the effect of a known antiproliferative drug in a more than additive fashion relative to the activity of the chemopotentiator or antiproliferative agent used alone. In some cases, a chemosensitizing effect may be observed. This is defined as the effect of use of an agent that if used alone would not demonstrate significant antitumor effects but would improve the antitumor effects of an antiproliferative agent in a more than additive fashion than the use of the antiproliferative agent by itself.

As used herein, the term imidazoline includes all members of that chemical family including the forms and analogs thereof. The imidazoline family is defined by chemical structure as the ring structures previously described.

As used herein, antiproliferative agents are compounds, which induce cytostasis or cytotoxicity. Cytostasis is the inhibition of cells from growing while cytotoxicity is defined as the killing of cells. Specific examples of antiproliferative agents include: antimetabolites, such as methotrexate, 5-fluorouracil, gemcitabine, cytarabine; anti-tubulin protein agents such as the vinca alkaloids, paclitaxel, colchicine; hormone antagonists, such as tamoxifen, LHRH analogs; and nucleic acid damaging agents such as the alkylating agents melphalan, BCNU, CCNU, thiotepa, intercalating agents such as doxorubicin and metal coordination complexes such as cisplatin and carboplatin.

DESCRIPTION OF PREFERRED EMBODIMENTS

Figure 1:
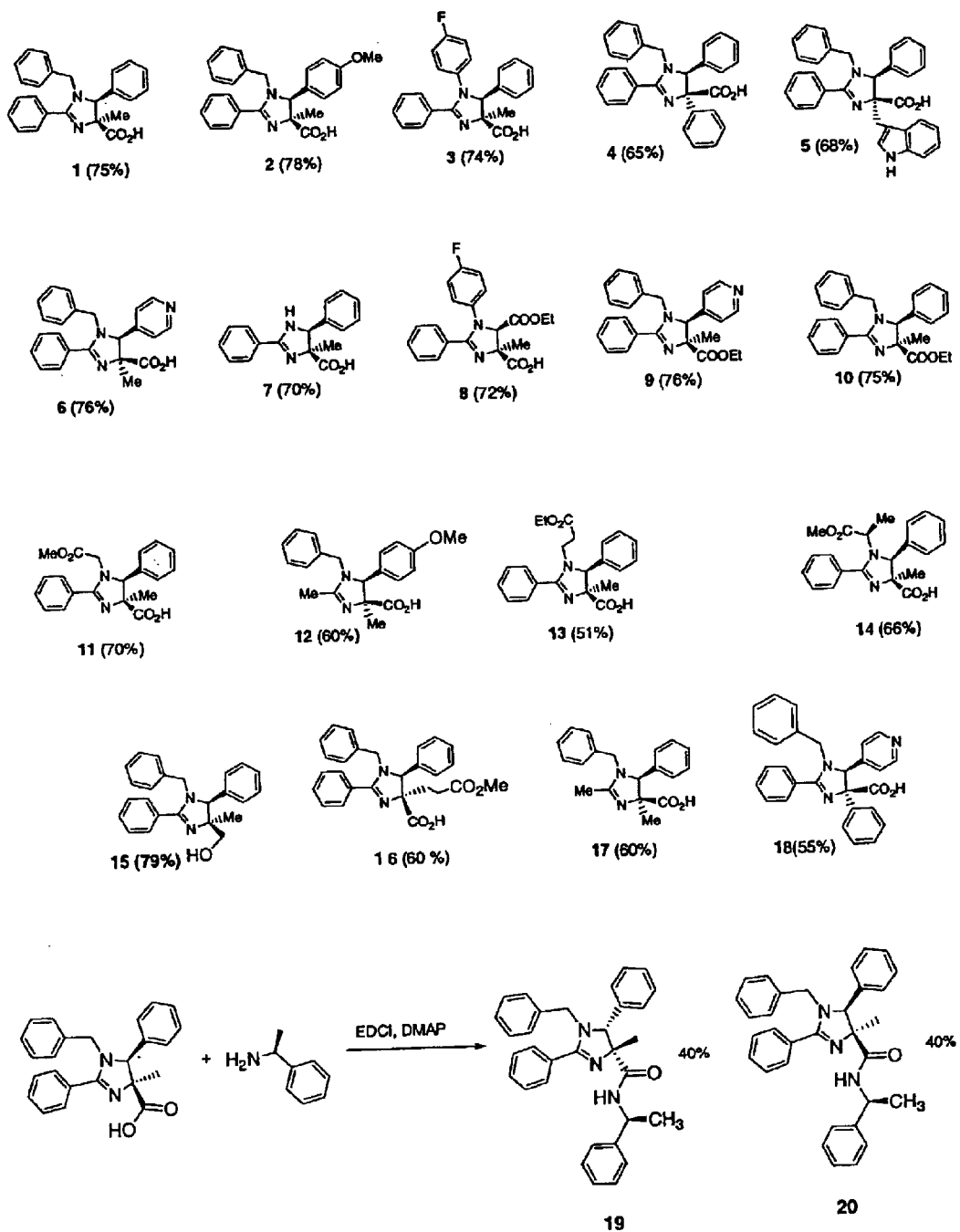
FIG. 1 shows the structures of compounds 1 to 20.
Figure 2:
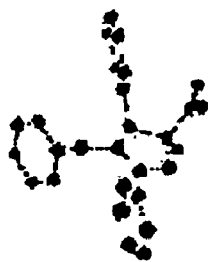
FIG. 2 shows the x-ray crystal structure of compound 1 which is representative.

A new class of imidazolines with anticancer (antitumor) anti-inflammatory activity and/or antimicrobial activity is described. Preferred compounds are shown in FIG. 1. The stereopositioning is shown in FIG. 2. The combination of these two key characteristics makes this class of imidazolines an extremely effective therapeutic drug to treat septic shock as well as many other inflammatory disorders such as asthma and infectious disorders. The objective of this invention is the use of multi-substituted imidazolines for therapeutic use as:

1) anti-inflammatory agents (for example in the treatment of asthma and rheumatoid arthritis).

2) antibacterial agents, including antiseptic agents.

The compounds of the present invention are very potent inhibitors of NF-κB in vitro (less than 0.1 microMolar concentrations) and preliminary experiments in cells have indicated that the compounds are not cytotoxic over a 72 hour time period. Several of the imidazolines indicated antimicrobial activity against several strains of bacteria with MIC's of 50 microgram/milliliter.

The present invention also relates to the synthesis of the first class of imidazoline-type NF-κB inhibitors anti-inflammatory agents. The imidazolines were prepared via a novel highly diastereoselective multicomponent synthesis using amino acid derived oxazolidinones as general templates.

The general procedure for synthesis of Imidazoline-4-carboxylic acids is as follows: A solution of aldehyde (for example 0.57 mmol), amine (for example 0.57 mmol) in dry $CH_2Cl_2$ (10 mL) was refluxed under $N_2$ for 2h. A solution of the oxazolone (for example 0.57 mmol) in dry $CH_2Cl_2$ (for example 5 mL) was added and the mixture was refluxed under $N_2$ for 6 h and then stirred overnight at room temperature. The product was preferably either precipitated out from 1:1 $CH_2Cl_2$ or isolated after silica gel chromatography with 4:1 EtOAc/MeOH.

This is a novel highly diastereoselective multicomponent one-pot synthesis of aryl, acyl, alkyl and heterocyclic unsymmetrical substituted imidazolines. After screening a small number of Lewis acids it was found that TMSCl (trimethylsilylchloride) promotes the condensation of azlactones and imines to afford imidazolines in good yields as single diastereomers (Scheme 1).

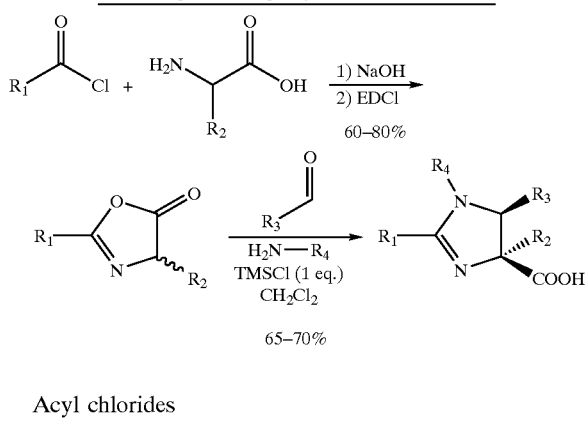

Scheme 1.
Multicomponent one-pot synthesis of imidazolines.

Acyl chlorides

where R is chiral can be used to obtain a single enantiomer. The azlactones were prepared from different N-acyl-α- amino acids followed by EDCI (1-(3-dimethylaminopropyl)-3-ethylcarbodiimide hydrochloride) mediated dehydration to provide the pure azlactones in high yields (Schunk, S., et al., Organic letters 2, 907–910 (2000); and Sain, B., et al., Heterocycles 23 1611–1614 (1985)). The cycloaddition reactions with the imines proceeded well at slightly elevated temperatures (for example 40° C.) to provide the high substituted imidazolines in good yields. The absence of trimethylsilyl chloride resulted in the formation of β-lactams, presumably via a ketene intermediate(S. Peddibhotla, S. Jayakumar and J. J. Tepe, Highly Diastereoselective Multicomponent Synthesis of Unsymmetrical Imidazolines, *Organic Letters* 4, 3533–3535 (2002)). Only the trans diastereomers of the imidazolines were observed in all of these reactions as determined by NOE experiments and X-ray crystallography. The diastereoselective multicomponent one-pot synthesis provided a wide range of aryl, acyl, alkyl and heterocyclic substituted imidazolines in excellent yields (Table 1).

TABLE 1

| compound | $R_1$ | $R_2$ | $R_3$ | $R_4$ | $R_5$ | Yield (%) |
|---|---|---|---|---|---|---|
| 1 | Phenyl | Methyl | Phenyl | Benzyl | H | 75 |
| 2 | Phenyl | Methyl | 4-methoxy-phenyl | Benzyl | H | 78 |
| 3 | Phenyl | Methyl | Phenyl | 4-Fluoro-phenyl | H | 74 |
| 4 | Phenyl | Phenyl | Phenyl | Benzyl | H | 65 |
| 5 | Phenyl | 1H-indol-3-yl-methyl | Phenyl | Benzyl | H | 68 |

TABLE 1-continued

| compound | $R_1$ | $R_2$ | $R_3$ | $R_4$ | $R_5$ | Yield (%) |
|---|---|---|---|---|---|---|
| 6 | Phenyl | methyl | pyridin-4-yl | Benzyl | H | 76 |
| 7[a] | Phenyl | Methyl | Phenyl | H | H | 70 |
| 8 | Phenyl | Methyl | Ethoxy-carbonyl | H | H | 72 |
| 9[b] | Phenyl | Methyl | pyridin-4-yl | Benzyl | Et | 76 |
| 10[c] | Phenyl | Methyl | Phenyl | Benzyl | Et | 75 |

Table 1.
Preparation of imidazolines 1–10.
[a]After Hydrogenation (10% Pd/C, $H_2$ 1 atm) of compound 1,
[b]After esterfication (SOCl2, EtOH) of compound 6,
[c]After esterfication (SOCl2, EtOH) of compound 1.

While the complete mechanistic detail of this process is still under investigation, the reaction does not seem to proceed by activation of the carbonyl oxygen of the oxazolone by trimethylsilyl chloride, in turn causing ring-opening to the intermediate nitrilium ion as initially expected (Ivanova, G. G., Tetrahedron 48 177–186 (1992)). Carrying out the condensation in presence of slight excess of triethylamine halted the reaction altogether suggesting that acidic conditions were required. In addition, the addition of Lewis acids such as $TiCl_4$ or $BF_3$. $OEt_2$ did not result in any product formation. In the light of these findings, it is proposed that the reaction probably proceeds by 1,3-dipolar type of cycloaddition. Steric repulsion between the $R_2$ and $R_3$ moieties during the cycloaddition can explain the diastereoselectivity (Scheme 2).

Scheme 2.
Proposed mechanism for imidazoline formation.

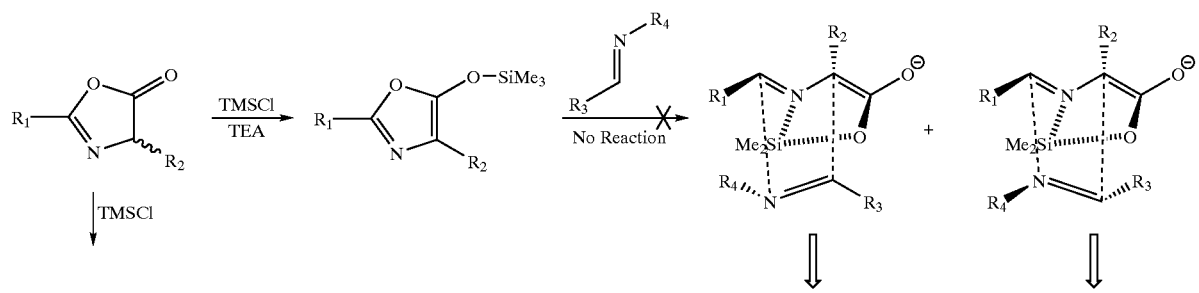

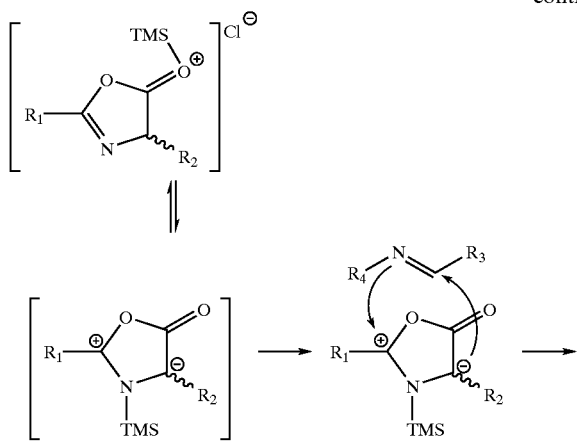
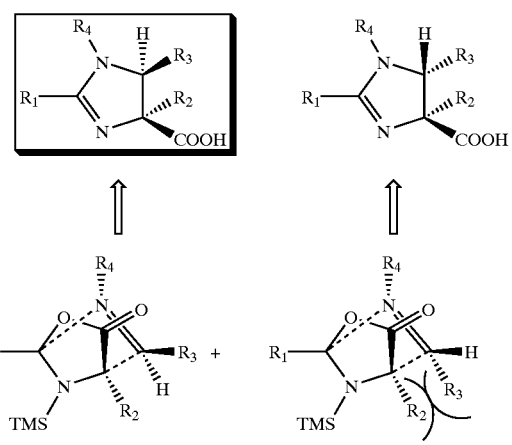

EXAMPLES 1–20
Experimental Section
1. Dl -(3S, 4S)-1-Benzyl-4-methyl-2,5-diphenyl-4,5-dihydro-1H-imidazole-4-carboxylic acid SP-1-61:

A solution of benzaldehyde (0.06 g, 0.57 mmol), benzylamine (0.061 g, 0.57 mmol) in dry dichloromethane (15 mL) was refluxed under nitrogen for 2 h. 2-Phenyl-4-methyl-4H-oxazolin-5-one (0.1 g, 0.57 mmol) and chlorotrimethylsilane (0.08 g, 0.74 mmol) were added and the mixture was refluxed under nitrogen for 6 h and then stirred overnight at rom temperature. The reaction mixture was evaporated to dryness under vacuum. The product was precipitated our as a white solid using 1:1 dichloromethane/hexanes mixture (0.155 g, 74%). $^1$H NMR (300 MHz) (DMSO-$d_6$): δ 1.8 (3H, s), 4.05 (1H, d, J=15 Hz), 4.95 (1H, d, J=14.8 Hz), 5.05 (1H, s), 7.05 (2H, s), 7.25–7.54 (8H, m), 7.74 (2H, t, J=7.2 Hz), 7.83 (1H, t, J=6.9 Hz), 8.0 (2H, d, J=8.4 Hz); $^{13}$C NMR (75 MHz) (DMSO-$d_6$): δ 25.2, 48.8, 70.4, 73.3, 122.3, 127.8, 128.3, 128.5, 128.9, 129.1, 129.3, 129.6, 129.7, 132.3, 133.2, 134, 166.1, 169.5; IR (neat): 3350 cm$^{-1}$, 1738 cm$^1$; HRMS (EI): calculated for $C_{24}H_{22}N_2O_2$ [M–H]$^+$ 369.1603, found [M–H]$^+$ 369.1610; M.P.: decomposes at 185–190° C.

2. dl-(3S, 4S)-1-Benzyl-5-(4-methoxyphenyl)-4-methyl-2-phenyl-4,5-dihydro-1H-imidazole-4-carboxylic acid SP-1-63: A solution of p-anisaldehyde (0.077 g, 0.57 mmol), benzylamine (0.061 g, 0.57 mmol) in dry dichloromethane (15 mL) was refluxed under nitrogen for 2 h. 2-Phenyl-4-methyl-4H-oxazolin-5-one (0.1 g, 0.57 mmol) and chlorotrimethyisilane (0.08 g, 0.74 mmol) were added and the mixture was refluxed under nitrogen for 6 h and then stirred overnight at room temperature. The reaction mixture was evaporated to dryness under vacuum. The product was precipitated out as a white solid using 1:1 dichloromethane/hexanes mixture (0.180 g, 78%). $^1$H NMR (300 MHz) (CDCl$_3$+2 drops DMSO-$d_6$): δ 1.8 (3H, s), 3.8 (3H, s), 3.95 (1H, d, J=15.3 Hz), 4.5 (1H, s), 4.9 (1H, d, J=15 Hz), 6.83–6.92 (4H, m), 7.08–7.19 (3H, m), 7.3–7.4 (3H) dd, J$_1$=5.1 Hz, J$_2$=1.8 Hz), 7.54–7.62 (2H, t, J=7.2 Hz), 762–7.68 (1H, t, J=7.2 Hz), 7.9 (2H, d, J=6.9 Hz); $^{13}$C NMR (75 MHz) (CD$_3$OD): δ 25.3, 48.8, 55.6, 70.9, 74.1, 115.2, 122.2, 123, 125.5, 127.9, 128.4, 129.2, 129.3, 129.6, 129.9, 132.8, 134.2, 161.1, 166.3, 168.4; IR (neat): 3388 cm$^{-1}$ 1738 cm$^{-1}$; HRMS (EI): calculated for $C_{25}H_{24}N_2O_3$ [M–H]$^+$ 397.1709, found [M–H]$^+$ 399.1717; M.P.: decomposes at 205–208° C.

3. dl-(3S, 4S)-1-(4-Fluorophenyl)-4-methyl-2,5-diphenyl-4,5-dihydro-1H-imidazole-4-carboxylic acid SP-1-101: A solution of benzaldehyde (0.060 g, 0.57 mmol), 4-fluoroaniline (0.063 g, 0.57 mmol) in dry dichloromethane (15 mL) was refluxed under nitrogen for 2 h. 2-Phenyl-4-methyl-4H-oxazolin-5-one (0.1 g, 0.57 mmol) and chlorotrimethylsilane (0.08 g, 0.74 mmol) were added and the mixture was refluxed under nitrogen for 6 h and then stirred overnight at room temperature. The reaction mixture was evaporated to dryness under vacuum. The product was precipitated out as a white solid using 1:1 dichloromethane/hexanes mixture (0.160 g, 74%). $^1$H NMR (300 MHz) (DMSO-$d_6$): δ 1.98 (3H, s), 5.98 (1H, s), 7.05–7.65 (14H, m); $^{13}$C NMR (75 MHz) (DMSO-$d_6$) δ 25.2, 71.2, 77.9, 116.9, 117, 117.1, 117.3, 123, 125.1, 125.3, 129.3, 129.4, 129.6, 130.1, 130.3, 130.4, 130.5, 132.5, 133.3, 134.5, 160.4, 163.7, 165.3, 170.4; IR (neat): 3450 cm$^{-1}$, 1744 cm$^{-1}$. HRMS (EI): calculated for $C_{23}H_{19}FN_2O_2$ [M–H]$^+$ 373.1352, found [M–H]$^+$ 373.1359; M.P.: decomposes at 230–232° C.

4. dl-(3S, 4S)-1-Benzyl-2,4,5-triphenyl-4,5-dihydro-1H-imidazole-4-carboxylic acid SP-1-125: A solution of benzaldehyde (0.6 g, 5.7 mmol), benzylamine (0.61 g, 5.7 mmol) in dry dichloromethane (120 mL) was refluxed under nitrogen for 2 h. 2,4-Diphenyl-4H-oxazolin-5-one (1.35 g, 5.7 mmol) and chlorotrimethylsilane (0.8 g, 7.4 mmol) were added and the mixture was refluxed under nitrogen for 6 h and then stirred overnight at room temperature. The product was purified by silica-gel column chromatography with 1:5 ethanol/ethyl acetate to afford 2.1 g of product in 65% yield as an off-white solid. $^1$H NMR (300 MHz) (CDCL$_3$): δ 3.8 (1H, d, J=15.6 Hz), 4.62 (1H, d, J=15.6 Hz), 4.98 (1H, s), 6.58 (2H, d, J=8.1 Hz), 7.05–7.65 (16H, m), 7.9 (2H, d, J=7.2 Hz); $^{13}$C NMR (75 MHz) (CDCl$_6$) δ 29.7, 48.3, 75.6, 79.1, 123.1, 125.7, 126.7, 127.3, 127.4, 127.9, 128.1, 128.2, 128.8, 128.9, 129, 129.3, 132.9, 133.8, 136, 143.1, 164.8, 168.1; IR (neat): 3400 cm$^{-1}$ (very broad), 1738 cm$^{-1}$; HRMS (EI): calculated for $C_{29}H_{24}N_2O_2$ [(M–H) CO$_2$]$^+$ 387.1526 and observed [M–H]—CO$_2$]$^+$ 387.1539; M.P.: decomposes at 153–155° C.

5. dl-(3S, 4S)-1-Benzyl-4-(1H-indol-3-ylmethyl)-2,5-diphenyl-4,5-dihydro-1H-imidazole-4-carboxylic acid SP-1-128: A solution of benzaldehyde (0.6 g, 5.7 mmol), benzylamine (0.61 g, 5.7 mmol) in dry dichloromethane (120 mL) was refluxed under nitrogen for 2 h. 4-(1H-Indol-3-ylmethyl)-2-phenyl-4H-oxazol-5-one (1.65 g, 5.7 mmol) and chlorotrimethylsilane (0.8 g, 7.4 mmol) were added and the mixture was refluxed under nitrogen for 6 h and then stirred overnight at room temperature. The product was purified by silica-gel column chromatography with 1:5 ethanol/ethyl acetate to afford 3.1 g of product in 68% yield as an off-white solid. $^1$H NMR (300 MHz) (DMSO-$d_6$): δ 3.95 (1H, d, J=16.2 Hz), 4.6 (1H, d, J=16.2 Hz), 5.25 (1H, s), 6.1 (2H, d, J=7.8 Hz), 6.9–7.3 (5H, m), 7.3–8.0 (15H, m), $^{13}$C NMR (75 MHz) (DMSO-$d_6$) δ 169.6, 166, 136.5, 133.7, 132.5, 132.3, 129.7, 129.4, 128.9, 128.7, 128.6, 127.9, 127.8, 126.7, 126.6, 122.7, 121.4, 119, 111, 105.8, 74.4, 70.4, 48.5, 32.3; IR (neat): 3420 cm$^{-1}$ (very broad), 1741 cm$^{-1}$; HRMS (EI); calculated for $C_{32}H_{27}N_3O_2$ [M–H]$^+$ 484.2025 and observed [M–H]$^+$ 484.2011; M.P.: decomposes at >250° C.

6. dl-(3S, 4S)-1-Benzyl-4-methyl-2-phenyl-5-pyridin-4yl-4,5-dihydro-1H-imidazole-4-carboxylic acid SP-1-150: A solution of pyridin-4-carboxalaldehyde (0.061 g, 0.57 mmol), benzylamine (0.061 g, 0.57 mmol) in dry dichloromethane (15 mL) was refluxed under nitrogen for 2 h. 2-Phenyl-4-methyl 4H-oxazolin-5-one (0.1 g, 0.57 mmol) and chlorotrimethylsilane (0.08 g, 0.74 mmol) were added and the mixture was refluxed under nitrogen for 6 h and then stirred overnight at room temperature. The reaction mixture was evaporated to dryness under vacuum. The product was isolated using 4:1 ethyl acetate/methanol as an off-white solid (0.161 g, 76%). $^1$H NMR (300 MHz) (DMSO-$d_6$): δ 1.8 (3H, s), 4.24 (1H, d, J=15.9 Hz), 4.9 (1H, d, J=14.8 Hz), 5.15 (1H, s), 7.0–7.15 (2H, m), 7.25–7.35 (3H, m), 7.45–7.5 (2H, m), 7.7–7.9 (3H, m), 7.95–8.05 (2H, m), 8.6–8.7 (2H, m); $^{13}$C NMR (75 MHz) (DMSO-$d_6$) δ 25.1, 49.1, 70.6, 71.7, 122.1, 123, 127.9, 128.4, 128.8, 129.2, 129.4, 132.8, 133.9, 141.4, 149.8, 166.5, 169.05; IR (neat); 3400 cm$^{-1}$, 1746 cm$^{-1}$; HRMS (EI): calculated for $C_{23}H_{21}N_3O_2$ [M–H]$^+$ 370.1556, found [M–H]$^+$ 370.1556; M.P.: decomposes at 185–190° C.

7. dl (3S, 4S)-4-Methyl-2,5-diphenyl-4,5-dihydro-1H-imidazole-4-carboxylic acid: 16/17 [JK-1-135] To a well-stirred suspension of imidazoline-4-carboxylic acid 10 (0.1 gm, 0.27 mmol) and cyclohexene (0.1 ml, 1.25 mmol) in dry THF (30 ml) added 10% Pd/C (45 mg, 0.06 mmol). The suspension was refluxed for 36 h. The reaction mixture cooled to room temperature and ethanol (10 mL) was added. The mixture was filtered through a Celite bed, washed with ethanol and the filtrate was evaporated under reduced pressure. The crude product was purified by column silica-gel chromatography using ethanol, to yield a white solid (0.070 g, 93%). $^1$H NMR (300 MHz) (DMSO-$d_6$) δ 1.76 (s, 3H), 5.34 (s, 1H), 7.34–7.36 (b, 5H), 7.69 (dd, J=8.1, 7.2, 2H), 7.81 (1H, dd, $J_1$=6.9 Hz and $J_2$=7.2 Hz), 8.15 (2H, d, J=8.4 Hz); $^{13}$C NMR (75 MHz) (DMSO-$d_6$): 25.32, 55.66, 70.79, 72.57, 123.12, 128.24, 128.96, 129.42, 129.67, 130.12, 135.42, 136.24, 164.24, 170.77; IR (neat) 1734 cm$^-$, 1616 cm$^-$; MS (EI): calculated for $C_{17}H_{16}N_2O_2$ (m/z) 280.12 observed m/z: 280.1; M.P.: decomposes at 222–224° C.

8. dl-(3S, 4S)-1-(4-Fluorophenyl)-4-methyl-2-phenyl-4,5-dihydro-1H-imidazole-4,5-dicarboxylic acid 5-ethyl ester SP-1-175: A solution of ethyl glyoxalate (0.058 g, 0.57 mmol) as 50% solution in toluene (1.03 g/ml), 4-fluoroaniline (0.063 g, 0.57 mmol) in dry dichloromethane (15 mL) was refluxed under nitrogen for 2 h. 2-Phenyl-4-methyl-4H-oxazolin-5-one (0.1 g, 0.57 mmol) and chlorotrimethylsilane (0.08 g, 0.74 mmol) were added and the mixture was refluxed under nitrogen for 6 h and then stirred overnight at room temperature. The reaction mixture was evaporated to dryness under vacuum. The product was purified by silica-gel column chromatography using 4:1 ethyl acetate/methanol, to yield a white solid (0.152 g, 72%). $^1$H NMR (300 MHz) (CD$_3$OD): δ 1.2 (3H, t, J=7.2 Hz), 2.03 (3H, s), 4.9 (2H, dq, $J_1$=7.2 Hz, $J_2$=2.1 Hz), 5.48 (1H, s), 7.1–7.8 (9H, m); $^{13}$C NMR (75 MHz) (CD$_3$OD): δ 169.9, 166.2, 164.0, 162.1, 134.4, 131.5, 129.7, 129.6, 129.5, 129.3, 121.8, 116.9, 116.7, 75.1, 69.1, 62.9, 24.2, 12.8; 1R (neat): 3450 cm$^{-1}$, 1743 cm$^{-1}$; HRMS (EI): calculated for $C_{20}H_{19}FN_2O_4$ [M–H]$^+$ 369.1251, and observed [M–H]$^+$ 369.1255; M.P.: decomposes at 190–193° C.

9. dl-(3S, 4S)-1-Benzyl-4-methyl-2-phenyl-5-pyridin-4-yl-4,5-dihydro-1H-imidazole-4-carboxylic acid ethyl ester JK-1-183: To a well-stirred suspension of dl-(3S, 4S)-1-Benzyl-4-methyl-2-phenyl-5-pyridin-4yl-4,5-dihydro-1H-imidazole-4-carboxylic acid 12 (0.1 g, 0.27 mmol) in dry dichloromethane (30 mL) at 0° C. added a solution of oxallyl chloride (0.14 g, 1.1 mmol) in dry dichloromethane (5 mL). A solution of DMF (0.001 mL) was added to the reaction mixture and was stirred at 0° C. for another 2 h. The dichloromethane was evaporated under vacuum and the reaction mixture cooled to 0° C. after which absolute ethanol (20 mL) was added. The solution was allowed to stir for an additional 1 h. The solvent was evaporated under vacuum and the reaction mixture diluted with dichloromethane (30 mL) and washed with saturated sodium bicarbonate (1–0 mL) and water (10 mL). The organic layer was dried over sodium sulfate and was concentrated under vacuum to yield crude product, which was further purified by silica-gel column chromatography using ethyl acetate, to yield a pale yellow oil (0.097 gm, 91%). $^1$H NMR (300 MHz) (CDCl$_3$): δ 0.86 (3H, t, J=7.2 Hz), 1.57 (3H, s), 3.64 (2H, q, J=7.2 Hz), 3.83 (1H, d, J=15.3 Hz), 4.27 (1H, s), 4.77 (1H, d, J=15.3, Hz), 6.97 (2H, dd, $J_1$=7.2 Hz and $J_2$=2.4 Hz), 7.22–7.54 (6H, m), 7.31–7.54 (2H, m), 7.78–7.81 (2H, m), 8.59–8.61 (2H, m). $^{13}$C NMR (75 MHz) (CDCl$_3$): δ 13.45, 27.13, 49.47, 60.83, 71.87, 77.94, 122.56, 127.79, 127.93, 128.55, 128.70, 130.21, 130.51, 135.82, 146.59, 149.75, 166.02, 171.37; IR (neat): 1734 cm$^{-1}$; MS (EI): calculated for $C_{25}H_{26}N_2O_2$ (m/z) 399.19 observed m/z: 399.3.

10. dl-(3S, 4S)-1-Benzyl-4-methyl-2,5-diphenyl-4,5-dihydro-1H-imidazole-4-carboxylic acid ethyl ester JK-1-186: To a well-stirred suspension of Imidazoline-4-carboxylic acid 10 (0.1 gm, 0.27 mmol) in dry methylene chloride (30 ml) at 0° C. added a solution of oxallyl chloride (0.14 g, 1.1 mmol) in dry dichloromethane (5 ml). A solution of DMF (0.001 mL) in dry dichloromethane (1 mL) was added to the reaction mixture and was stirred at 0° C. for another 2 h. The dichloromethane was evaporated under vacuum and the reaction mixture cooled to 0° C. after which absolute ethanol (20 ml) was added. The solution was allowed to stir for an additional 1 h. The solvent was evaporated under vacuum and the reaction mixture diluted with dichloromethane (30 ml) and washed with saturated sodium bicarbonate (10 ml) and water (10 ml). The organic layer was dried over sodium sulfate and was concentrated under vacuum to yield crude product, which was further purified by silica-gel column chromatography using ethyl acetate, to yield colorless oil (0.095 gm, 89%). $^1$H NMR (300 MHz, CDCl$_3$): δ 0.84 (3H, t, J=7.2 Hz), 1.57 (3H, s), 3.60 (2H, q, J=7.2 Hz), 3.85 (1H, d, J=15.3 Hz), 4.32 (1H, s), 4.74 (1H, d, J=15.3 Hz), 6.98 (2H, dd, $J_1$=6.9 Hz and $J_2$=2.1 Hz), 7.27–7.35 (m, 8H), 7.49–7.51 (2H, m), 7.76–7.79 (2H, m); $^{13}$C NMR (75 MHz, CDCl$_3$): δ 13.80, 27.13, 49.12, 60.06, 71.31, 127.98, 128.03, 128.12, 128.67, 129.02, 129.11, 130.96, 136.40, 136.80, 166.11, 171.78; IR (neat); 1730 cm$^{-1}$, 1495 cm$^{-1}$; MS (EI): calculated for $C_{26}H_{26}N_2O_2$ (m/z) 398.2 observed m/z=398.9.

11. dl-(3S, 4S)-1-Methoxycarbonylmethyl-4-methyl-2,5-diphenyl-4,5-dihydro-1H-imidazole-4-carboxylic acid JK-1-199: To a well stirred solution of 2-Phenyl-4-methyl-4H-oxazolin-5-one (0.5 g, 2.85 mmol) and TMSCl (0.37 g, 3.42 mmol) in dry dichloromethane (50 ml) added a solution of (Benzylidene-amino)-acetic acid methyl ester (0. gm, mmol) in dry methylene chloride (20 ml) and the mixture was refluxed under nitrogen for 10 h and then stirred overnight at room temperature. The reaction mixture was evaporated to dryness under vacuum. The product was precipitated out as a white solid using a 1:1 dichloromethane/hexanes mixture (0.70 g, 70%). $^1$H NMR (300 MHz) (CD$_3$OD): δ 1.99 (3H, (1H, d, J=18.3 Hz), 4.53 (1H, d, J=18.3 Hz), 5.39 (1H, s), 7.47–7.50 (5H, m), 7.74–7.87 (5H, m). $^{13}$C NMR (75 MHz) (CD$_3$OD): δ 24.23, 52.09, 70.83, 75.38, 121.84, 128.26, 128.69, 129.52, 129.75, 131.78, 134.02, 167.59, 168.62, 169.19; IR (neat): 3468 cm$^{-1}$, 1747 cm$^{-1}$; MS (EI): calculated for C$_{20}$H$_{20}$N$_2$O$_4$ (m/z) 352.14 observed m/z=353.2; M.P.: decomposes at 215–217° C.s), 3.67 (3H, s), 3.96.

12. 1-Benzyl-5-(4-methoxy-phenyl)-2,4-dimethyl-4,5-dihydro-1H-imidazole-4-carboxylic acid SP-1-189: A solution of p-anisaldehyde (1.4 g, 10.4 mmol), benzylamine (1.11 g, 10.4 mmol) in dry dichloromethane (150 mL) was refluxed under nitrogen for 2 h. 2,4-dimethyl-4H-oxazolin-5-one SP-1-188 (1f) (1 g, 8.7 mmol) and chlorotrimethylsilane (1.22 g, 11.3 mmol) were added and the mixture was refluxed under nitrogen for 6 h and then stirred overnight at room temperature. The reaction mixture was evaporated to dryness under vacuum. The product was precipitated out as a white solid using a 1:1 dichloromethane/hexanes mixture (1.9 g, 65%). $^1$H NMR (300 MHz) (CDCl$_3$): δ 1.13 (3H, s), 2.43 (3H, s), 3.83 (3H, s), 4.17 (1H, d, J=15.9 Hz), 4.57 (1H, d, J=15.9 Hz), 5.8 (1H, s) 6.92 (2H, d, J=8 Hz), 7.05 (2H, d, J=8 Hz) 7.2–7.4 (5H, m); $^{13}$C NMR (75 MHz) (CDCl$_3$): δ 12.3, 21.9, 47.8, 55.2, 70.4, 114.3, 125.2, 126.9, 128.5, 129.3, 133.3, 159.9, 163.2, 174.8; IR (neat): 3388 cm$^{-1}$; 1738 cm$^{-1}$; HRMS (EI): calculated for C$_{20}$H$_{22}$N$_2$O$_3$ [M−H]$^+$ (m/z)=337.1552, found (m/z) 337.1548.

13. dl-(3S, 4S)-1-(2-Ethoxycarbonyl-ethyl)-4-methyl-2,5-diphenyl-4,5-dihydro-1H-imidazole-4-carboxylic acid JK-1-215: To a well stirred solution of 2-Phenyl-4-dimethyl-4H-oxazolin-5-one (1.0 g, 5.7 mmol) and TMSCl (1 ml, 6.8 mmol) in dry dichloromethane (80 ml) added a solution of 3-(Benzylidene-amiono)-propionic acid ethyl ester (1.4 gm, 6.8 mmol) in dry methylene chloride (60 ml) and the mixture was refluxed under nitrogen for 10 h and then stirred overnight at room temperature. The reaction mixture was evaporoated to dryness under vacuum. The product was precipitated out as a white solid using a 1:1 dichloromethane/hexanes mixture (1.08 g, 51.4%). $^1$H NMR (500 MHz) (CD$_3$OD): δ 1.17 (t, J=7.5, 3H), 1.9 (s, 3H), 2.47–2.52 (m, 1H), 2.52–2.71 (m, 1H), 3.34–3.39 (m, 1H), 3.40–4.09 (m, 3H), 5.42 (s, 1H), 7.46–7.49 (m, 5H), 7.72–7.87 (m, 5H); $^{13}$C NMR (100 MHz) (CD$_3$OD): δ 13.35, 24.87, 30.64, 41.64, 61.00, 70.94, 73.51, 122.77, 128.99, 129.21, 129.80, 130.10, 132.78, 134.09, 167.32, 169.81, 170.9. IR (neat): 3481 cm$^{-1}$, 1743 cm$^{-1}$; MS (EI): calculated for C$_{22}$H$_{24}$N$_2$O$_4$ (m/z) 380.44 observed m/z=380.7. M.P.: decomposes at 218–220° C.

14. dl-(3S, 4S)-1-(1-Methoxycarbonyl-ethyl)-4-methyl-2,5-diphenyl-4,5-dihydro-1H-imidazole-4-carboxylic acid JK-1-192: To a well stirred solution of 2-Phenyl-4-methyl-4H-oxazolin-5-one (0.25 g, 1.5 mmol) and TMSCl (0.23 ml, 1.8 mmol) in dry dichloromethane (50 ml) added a solution of 2-(Benzlidene-amino)-propionic acid methyl ester (0.34 gm, 1.8 mmol) in dry methylene chloride (20 ml) and the mixture was refluxed under nitrogen for 10 h and then stirred overnight at room temperature. The reaction mixture was evaporated to dryness under vacuum. The product was precipitated out as a white solid using a 1:1 dichloromethane/hexanes mixture (0.340 g, 66%). $^1$H NMR (300 MHz) (CD$_3$OD): δ 1.19 (d, J=6.9, 3H), 2.06 (s, 3H), 3.38 (s, 3H), 4.89 (q, J=6.9, 1H), 544 (s, 1H), 7.43–7.46 (5H, m), 7.75–7.85 (5H, m). $^{13}$C NMR (75 MHz) (CD$_3$OD): δ 14.9, 25.6, 52.7, 56.7, 71.9, 72.5, 122.2, 128.8, 128.9, 129.6, 130.0, 134.5, 135.8, 169.2, 169.4, 170.4, IR (neat): 3431 cm$^{-1}$, 1740 cm$^{-1}$; MS (EI): calculated for C$_{21}$H$_{22}$N$_2$O$_4$ (m/z) 366.4 observed m/z=366.6. M.P.: decomposes at 222–226° C.

15. 1-Benzyl-4-methyl-2,5-diphenyl-4,5-dihydro-1H-imidazol-4-yl)-methanol 14 [JK-1-123]: To a well stirred suspension of Lithium aluminum hydride (0.12 gm, 0.3 mmol) in dry THF (5 ml) added a solution of 1-Benzyl-4-methyl-2,5-diphenyl-4,5-dihydro-1H-imidazole-4-carboxylic acid (0.1 gm, 0.27 mmol) in dry THF (5 ml) at 0° C. drop wise, stirred at same temperature for 15 min quenched with ice cold saturated ammonium chloride solution [Caution: Ammonium chloride solution kept at 0° C. for about 30 min.; and should be added with extreme care; highly exothermic reaction and the reaction mixture should be at 0° C.] then added about 10 ml of 10% HCl. The reaction mixture diluted with excess of ethyl acetate (100 ml) washed with water (20 ml) dried over anhydrous sodium sulfate, filtered through a fluted filter paper and the organic layer evaporated under reduced pressure to yield the crude product which was purified by column chromatography using ethyl acetate. Yield: 79%; viscous oil, IR (neat): 3314, 2928, 1643, 1516; δ H (300 MHz, CD$_3$Cl$_3$): δ 1.25 (s, 3H), 3.48 (d, J=12, 1H), 3.56 (d, J=11.8, 1H), 3.75 (d, 12.9, 1H), 3.87 (s, 1H), 3.94 (d, J=12.9, 1H), 7.28–7.54 (m, 13H), 7.77–7.79 (m, 2H), 8.06 (brs, 1H); δ C (75 MHz, CDCl$_3$): δ 17.25, 51.67, 61.54, 66.28, 66.93, 127.266, 127.68, 128.26, 128.56, 128.82, 129.06, 131.77, 135.48 138.03, 139.90, 167.91; m/z: 357.2.

16. 1-Benzyl-4-(2-methoxycarbonyl-ethyl)-2,5-diphenyl-4,5-dihydro-1H-imidazole-4-carboxylic acid SP-1-201: A solution of benzaldehyde (0.252 g, 2.4 mmol), benzylamine (0.258 g, 2.4 mmol) in dry dichloromethane (100 mL) was refluxed under nitrogen for 2 h. 3-(5-Oxo-2-phenyl-4,5-dihydro-oxazol-4-yl)-propionic acid methyl ester SP-1-182 (1e)(0.5 g, 2 mmol) and chlorotrimethylsilane (0.282 g, 2.6 mmol) were added and the mixture was refluxed under nitrogen for 6 h and then stirred overnight at room temperature. The reaction mixture was evaporated to dryness under vacuum. The product was precipitated out as a white solid using a 1:1 dichloromethane/hexanes mixture (0.54 g, 60%). $^1$H NMR (300 MHz) (CDCl$_3$): δ 2.05–2.25 (2H, m), 2.3–2.5 (2H, m), 3.55 (3H, s), 4.38 (2H, ddd, J$_1$=4 Hz, J$_2$=9 Hz, J$_3$=25 Hz), 4.86 (1H, q, J=3.3), 7.1–7.6 (12H, m), 7.7–7.9 (4H, m); $^{13}$C NMR (75 MHz) (CDCl$_3$): δ 27.6, 30.1, 43.3, 51.6, 52.7, 127.1, 127.2, 127.3, 128.2, 128.3, 131.5, 131.6, 133.3, 137.8, 167.5, 171.4, 173.6; IR (neat): 1734 cm$^{-1}$, 1653 cm$^{-1}$; MS (EI): calculated for C$_{24}$H$_{22}$N$_2$O$_2$ (m/z) 442.5, found (m/z) 443.

17. dl-(3S, 4S)-1-Benzyl-2,4-dimethyl-5-phenyl-4,5-dihydro-1H-imidazole-4-carboxylic acid: 15[JK-1-238]. To a well stirred solution of 2,4-dimethyl-4H-oxazolin- 5-one (0.4 g, 3.5 mmol) and TMSCl (0.58 ml, 4.2 mmol) in dry dichloromethane (60 ml) added a solution of Benzyl-benzylidene-amine (0.82 gm, 4.2 mmol) in dry methylene chloride (40 ml) and the mixture was refluxed under nitrogen for 10 h and then stirred overnight at room temperature. The reaction mixture was evaporated to dryness under vacuum. The product was precipitated out as a white solid using a 1:1 dichloromethane/hexanes mixture (0.60 g, 60%). $^1$H NMR (300 MHz) (CD$_3$OD): δ 1.11 (s, 3H), 2.47 (s, 3H), 4.17 (d, J=16.2, 1H), 4.63 (q, J=16.2, 1H), 5.84 (s, 1H), 7.04–7.07 (m, 2H), 7.27–7.42 (m, 7H). $^{13}$C NMR (75 MHz) (CD$_3$OD): δ 12.62, 22.12, 48.27, 70.39, 71.25, 127.31, 128.83, 129.28, 129.58, 133.40, 133.46, 164.12, 175.19. IR (neat) 3431 cm$^{-1}$, 1740 cm$^{-1}$; MS (EI); calculated for C$_{19}$H$_{20}$N$_2$O$_2$ (m/z) 308.37 observed m/z=308.3, M.P.; decomposes at 232–234° C.

18. dl-(3S, 4S)-1-Benzyl-2,4-diphenyl-5-pyridin-4-yl-4,5-dihydro-1H-imidazole-4-carboxylic acid SP-1-195: A solution of pyridin-4-carboxylaldehyde (0.61 g, 0.57 mmol), benzylamine (0.61 g, 5.7 mmol) in dry dichloromethane (120 mL) was refluxed under nitrogen for 2 h. 2,4-Diphenyl-4H-oxazolin-5-one (1.35 g, 5.7 mmol) and chlorotrimethylsilane (0.8 g, 7.4 mmol) were added and the mixture was refluxed under nitrogen for 6 h and then stirred overnight at room temperature. The product was purified by precipitation from dichloromethane/ether mixture to afford 1.35 g of the product in 55% yield as an off-white solid. $^1$H NMR (300 MHz) (CDCl$_3$): δ 4 (1H, d, J=15.6 Hz), 5.0 (1H, d, J=15.6 Hz), 5.38 (1H, s), 7.1–7.65 (17H, m), 8.5 (2H, d, J=7.2 Hz); $^{13}$C NMR (75 MHz) (CDCl$_3$): δ 45.2, 66.3, 75.6, 123.7, 126.5, 126.9, 128.5, 128.6, 128.8, 129.2,, 129.3, 131.9, 133.5, 134.4, 136.2, 143.4, 149.7, 166.6, 166.9; IR (neat): 3400 cm$^{-1}$ (very broad), 1733 cm$^{-1}$; MS (EI): calculated for C$_{24}$H$_{22}$N$_2$O$_2$ (m/z) 434.34, found (m/z) 434.2.

Compounds 19 and 20. Synthesis of 1-Benzyl-4-methyl-2,5-diphenyl-4,5-dihydro-1H-imidazole-4-carboxylic acid (1-phenyl-ethyl)-amide from 1-Benzyl-4-methyl-2,5-diphenyl-4,5-dihydro-1H-imidazole-4-carboxylic acid: JK-1-309

To a well-stirred suspension of 1-Benzyl-4-methyl-2,5-diphenyl-4,5-dihydro-1H-imidazole-4-carboxylic acid (1.0 g, 0.27 mmol) in dry methylene chloride (25 ml), (S)-(–)-1-Phenyl-ethylamine (0.36 g, 29 mmol) was added EDCI-HCl (0.57 g, 29 mmol), after five minutes added a solution of DMAP (0.35 gm, 29 mmol) in methylene chloride (10 ml) and stirred for 5–6 hrs. The reaction mixture was washed with water (2×10 ml), saturated sodium bicarbonate (20 ml), water (20 ml), 2N HCl (20 ml) and then with water (30 ml). The organic layer dried over sodium sulfate and evaporated under reduced pressure. The crude product was purified by column silica-gel chromatography using ethyl acetate hexane mixture (1:1).

19: Yield (0.26 g, 40.7%). {[α]$_D$=+41.5°)} $^1$H NMR (300 MHz): δ 1.02 (d, J=6.9, 3H), 1.56 (s, 3H), 3.85 (d, J=15.6, 1H), 4.40 (s, 1H), 4.66 (d, J=15.6, 1H), 4.72 (t, J=6.9, 1H), 7.07–7.09 (m, 2H), 7.17–7.55 (m, 16H), 7.69–7.73 (m, 2H); $^{13}$C NMR (75 MHz): 21.39, 27.56, 48.09, 48.73, 72.66, 126.52, 127.24, 127.71, 127.99, 128.42, 128.57, 128.67, 128.95, 129.01, 129.14, 130.75, 130.82, 137.38, 137.60, 143.29, 165.44, 171.61.

20: (0.24 g, 38%). {[α]$_D$=37.7°)} $^1$H NMR (300 MHz): δ 1.40 (d, J=7.2 3H), 1.61 (s, 3H), 3.77 (d, J=15.6, 1H), 4.37 (s, 1H), 4.60 (d, J=15.6, 1H), 4.75 (t, J=7.5, 1H), 6.922–7.090 (m, 2H), 7.11–7.22 (m, 13H), 7.507–7.529 (m, 3H), 7.651–7.682 (m, 2H); $^{13}$C NMR (75 MHz): 21.58, 28.08, 47.97, 48.59, 72.62, 126.66, 126.99, 127.200, 127.69, 127.96, 128.21, 128.51, 128.58, 128.64, 129.13, 129.122, 130.70, 130.83, 137.184, 137.22, 143.28, 165.35, 171.62.

EXAMPLE 11

All compounds were evaluated for their potential anti-inflammatory activity by examining the activity of NF-κB in vitro in nuclear extracts using the procedure from Breton and Charbot-Fletcher (Breton, J. J., et al., J. Pharmacol Exp Ther 282 459–466 (1997)). Briefly, Human Jurkat leukemia T-cells (clone E6-1; Amer. Type Culture Collection, Rockville, Md.) are grown in RPMI-1640 Media (Gibco-BRL, Rockville, Md.) supplemented with 10% Fetal Bovine Serum, Penicillin (614 μg/mL), Streptomycin (10 μg/mL) and Hepes Buffer, pH 7.2 at 37° C., 5% CO$_2$. The Jurkat cells (1×10$^7$ cells/mL) are subsequently treated with various concentrations of imidazoline for 30 min. at 37° C. followed by PMA stimulation (5.0 ng/mL) for an additional 5 hours. Nuclear extracts are incubated for 20 minutes with a double stranded Cy3 labeled NF-κB consensus oligonucleotide, 5'-AGTTGAGGGGACTTTCCCAGGC-3' at room temperature. The crude mixture is loaded on a 5% non-denaturing polyacrylamide gel prepared in 1× Tris borate/EDTA buffer and electrophoresed at 200 V for 2 hours. After electrophoresis the gel is analyzed using a phosphorimager (Biorad FX plus) for detection of the NF-κB-DNA binding.

Figure 3:
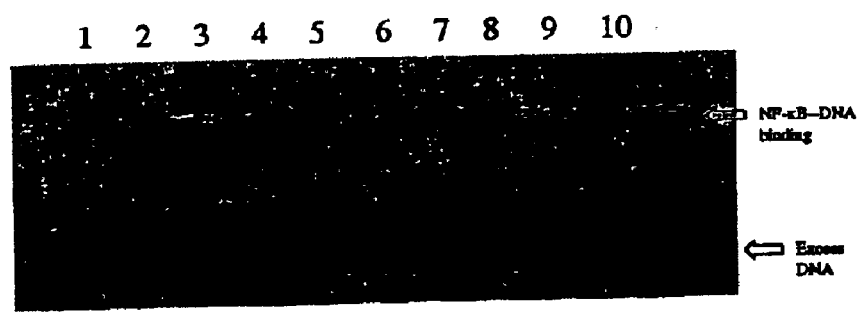
FIG. 3 is a EMSA of nuclear extracts with imidazolines 8 to 10. Lane 1, DNA only (control); lane 2, DNA, nuclear extract (10 μg) with p50 homodimer (control); lane 3, DNA, nuclear extract (10 μg) with PMA activation (control); lane 4, DNA, nuclear extract (10 μg) with no PMA activation (control); lane 5, DNA, nuclear extract (10 μg) after PMA activation with compound 8 (1.0 μM); lane 6, DNA, nuclear extract (10 μg) after PMA activation with compound 8 (0.1 μM); lane 7, DNA, nuclear extract (10 μg) after PMA activation with compound 9 (1.0 μM); lane 8, DNA, nuclear extract (10 μg) after PMA activation with compound 9 (0.1 μM); lane 9, DNA, nuclear extract (10 μg) after PMA activation with compound 10 (0.1 μM); lane 10, DNA, nuclear extract (10 μg) after PMA activation with compound 10 (0.1 μM).

Treatment of the cells to the imidazolines exhibited a significant inhibition of nuclear NF-κB activity. FIG. 3 clearly illustrates a decrease of nuclear NF-κB-DNA binding by imidazolines 8 to 10 (FIG. 3, lanes 5–10).

Cells treated with the imidazolines exhibited a significant inhibition of nuclear NF-κB activity (FIG. 3). FIG. 3 clearly illustrates a significant decrease of nuclear NF-κB-DNA binding in the presence 100 nM concentration of imidazolines 8–10 (FIG. 3, lanes 5–10).

The apparent absence of a slow moving band in lane 5 is indicative of significant (94%) NF-κB inhibition by compound 8 at 1 micromolar concentration in Jurkat Leukemia T-cells. Lane 6 indicates 88% inhibition of NF-κB-DNA binding in the nucleus by 100 nanomolar concentrations of compound 8.

EXAMPLE 12

All compounds were tested for their ability to inhibit NF-κB and the collected data is shown in Table 2. Currently, the most active compound in the series is the heterocyclic imidazoline 9 which exhibited 88% inhibition of NF-κB at 100 nM concentrations. Preliminary results indicate that the imidazolines do not exhibit significant cytotoxicity for up to 72 hours.

TABLE 2

| compound | concentration | % inhibition |
|---|---|---|
| 1 | 1 μM | 19% |
| 2 | 1 μM | 68% |
| 3 | 1 μM | 35% |
| 4 | 1 μM | 65% |
| 5 | 1 μM | 0% |
| 6 | 0.1 μM | 84% |
| 7 | 0.1 μM | 38% |
| 8 | 0.1 μM | 88% |
| 9 | 0.1 μM | 71% |
| 10 | 0.1 μM | 22% |

Table 2. Inhibition of NF-κB by imidazolines 1–10. The most active compound in this series was compound 8.

$IC_{50}$ values in Mammalian Jurkat cells Leukemia T cells: $IC_{50}$ value is defined as the concentration of compounds at which 50% of the protein/enzyme is inhibited in cells.

TABLE 3

| Compound 1. | $IC_{50}$ = 1.95 micromolar |
| Compound 2. | $IC_{50}$ = 40 nanomolar |
| Compound 3. | $IC_{50}$ = 6.5 nanomolar |
| Compound 4. | $IC_{50}$ = 73 nanomolar |
| Compound 5. | $IC_{50}$ = Not tested |
| Compound 6. | $IC_{50}$ = 0.3 micromolar |
| Compound 7. | $IC_{50}$ = 20 nanomolar |

EXAMPLE 13

Compounds 4, 6 and 7 were tested for the inhibition of bacteria. A total of 9 bacterial strains were screened. The following Gram-negative and Gram-positive bacteria were included: *Staphylococcus aureus, Enterobacter aerogenes, Esherichia coli, Klebsiella pneumonia, Pseudomonas aeruginosa, Serratia marcescens, Bacillus cerius, Bacillus subtillus* and *micrococcus luteus*. Bacterial isolates were removed from storage, streaked on to nutrient agar plates and incubated for 18–24 hours at 35° C. A working bacterial suspension was prepared by suspending 3–5 isolated colonies in 5 mL saline solution. The turbidity of this suspension was carefully adjusted photometrically to equal that of a 0.5 McFarland standard. The zone diameters were determined by a standardized disk diffusion method using cation-supplemented Mueller-Hinton agar according to NCCLS guidelines (National Committee for Clinical Laboratory Standards. *Methods for dilution Antimicrobial Susceptibility Tests for Bacteria that Grow Aerobically*. Fifth Edition: Approved Standard M7-A5. Wayne, Pa.: NCCLS (2000)). Minimum inhibitory concentrations (MICs) were considered the lowest concentration that gave a clear zone of inhibition. The inoculated agar plates were incubated for 16–20 hours at 35° C. in ambient air. The diameters of the zones were read in millimeters. The results are shown in Table 4.

TABLE 4

| Microbe | MIC | |
|---|---|---|
| Compound 4 | | |
| *Bacillus subtillus* | 13 mm | 50 µg |
| *Bacillus cereus* | 11 mm | 50 µg |
| *Micrococcus luteus* | 12 mm | 200 µg |
| *Staphylococcus aureus* | 12 mm | 200 µg |
| Compound 6 | | |
| *Micrococcus luteus* | 10 mm | 200 ηg |
| Compound 7 | | |
| *Micrococcus luteus* | 10 mm | 56 ηg |

EXAMPLE 14
Treatment of Imidazoline in RIF-1 Murine Tumor Model

Several of the NF-κB inhibitors (compounds 1, 3, 4 and 6) were tested in animals. Tumor cells were injected, bilaterally, into the backs of mice. When tumors reached 100 mm³, the mice were treated with an intraperitoneal injection of the compound. Tumor volumes were measured 3 times a week until they reached 4 times the size they were on the first treatment day. Data is recorded as "Days to 4×' or ratio of 'Days to 4×" of the treated over untreated controls.

Figure 4A:
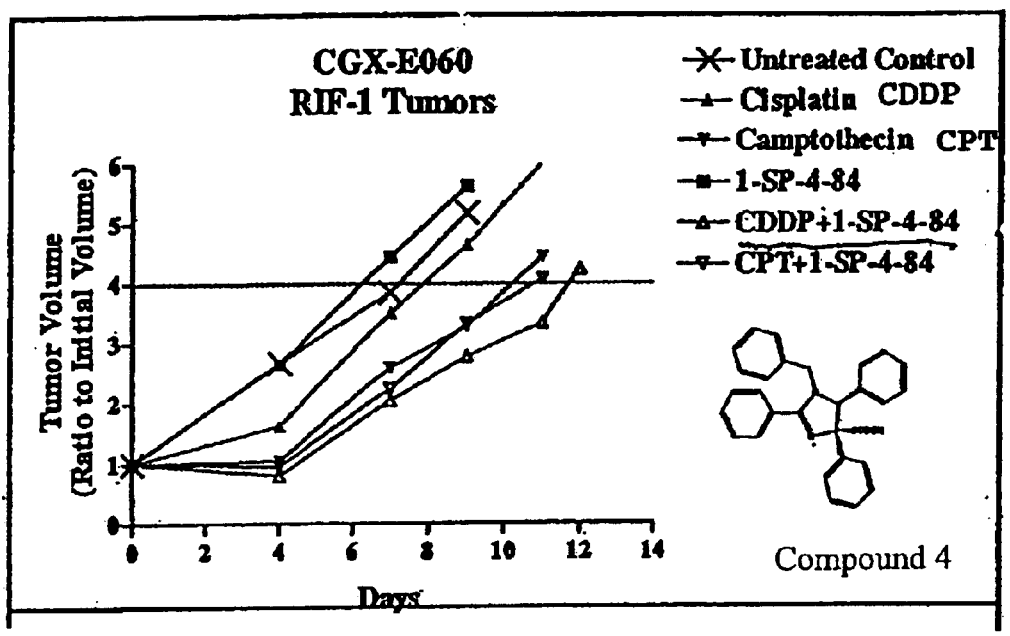
FIGS. 4A and 4B show tumor growth delay with compounds 4 and 6.

Combinational treatment of the mice with cis-platin (CDDP) and camptothecin (CPT) in the presence of compound 4 (1-SP-4-84) exhibited considerable chemopotentiation of cis-platin (FIG. 4A). In addition, this group had 4 of the 8 tumors that remained <4× its volume at day 22 of the experiment. No significant chemopotentiation of camptothecin in the presence of compound 4 was shown.

Figure 4B:
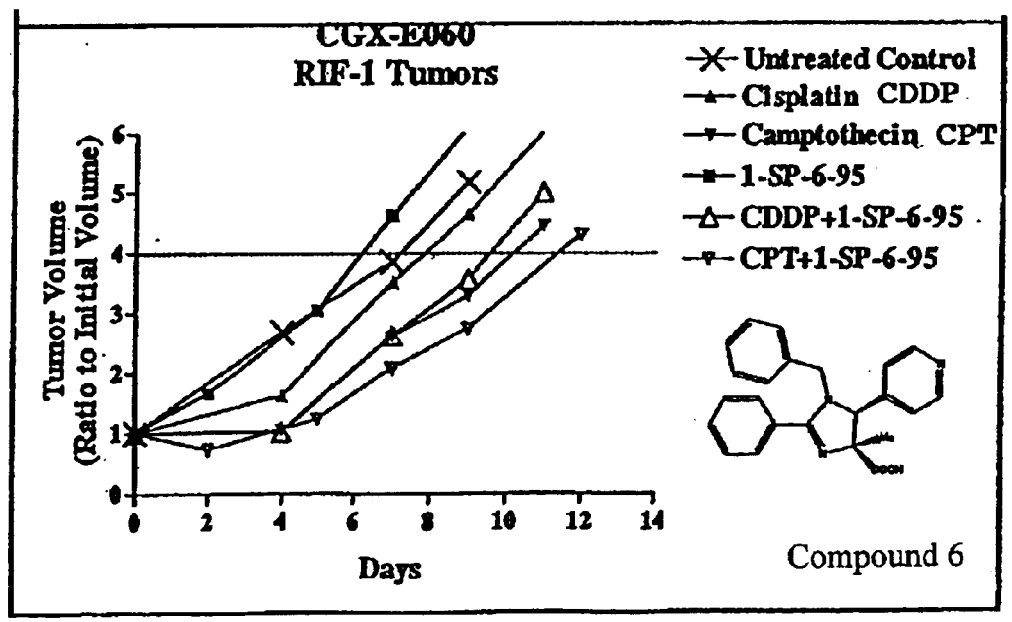

Compound 6 (1-SP-6-95) exhibited significant chemopotentiation of cis-platin as well as camptothecin (FIG. 4B). However, chemopotentiation by 6 was not as pronounced as seen with compound 4.

Combinational treatment of the mice with cis-platin (CDDP) and camptothecin (CPT) in the presence and absence of the imidazolines indicated that compounds 1 and 3 showed no significant chemopotentiation of either cis-platin or camptothecin (data not shown).

Combinational therapy of compound 4 with cis-platin showed a tumor growth delay (in days) of more than 10.26 days as compared to cis-platin (0.82 days) or camptothecin (3.79 days) alone (Table 5). In addition, half of the tumors in this RIF-1 murine model did not reach the 4× tumor volume cut-off point at day 22 days when exposed to combinational treatment with compound 4.

TABLE 5

Antitumor efficacy of imidazolines as measured
by the RIF-1 murine model of tumor growth delay.
CGX-E060

| Treatment | # of Tumors | Route | Dose (mg/kg) | Days to 4× (Ave ± SE) | T/C | Median | Days Delay |
|---|---|---|---|---|---|---|---|
| Untreated | 10 | — | — | 7.3 ± 0.6 | 0.0 | 7.0 | 0.00 |
| Cis-platin | 8 | IP | 4 | 8.1 ± 0.4 | 1.1 | 7.8 | 0.82 |
| Compound 1 | 8 | IP | 100 | 6.5 ± 0.3 | 0.9 | 6.4 | −0.57 |
| Compound 3 | 8 | IP | 100 | 7.6 ± 1.0 | 1.0 | 6.8 | −0.20 |
| Compound 4 | 6/8 | IP | 100 | 6.4 ± 0.2 | 0.9 | 6.5 | −0.56 |
| Compound 6 | 8 | IP | 100 | 6.6 ± 0.3 | 0.9 | 6.6 | −0.41 |
| CDDP + 1 | 8 | IP | 4/100 | 8.8 ± 0.5 | 1.2 | 9.1 | 2.05 |
| CDDP + 3 | 8 | IP | 4/100 | 8.8 ± 0.3 | 1.2 | 8.5 | 1.49 |
| CDDP + 4* | 8 | IP | 4/100 | >17.1 ± 1.9 | >2.3 | >17.3 | >10.26 |
| CDDP + 6 | 8 | IP | 4/100 | 9.8 ± 0.3 | 1.3 | 10.1 | 3.09 |
| Camptothecin | 8 | IP | 6 | 10.3 ± 0.6 | 1.4 | 10.8 | 3.79 |
| CPT + 1 | 8 | IP | 6/100 | 10.2 ± 0.4 | 1.4 | 10.3 | 3.27 |
| CPT + 3 | 8 | IP | 6/100 | 8.8 ± 0.6 | 1.2 | 8.7 | 1.70 |
| CPT + 4 | 4/8 | IP | 6/100 | 10.8 ± 0.4 | 1.5 | 11.1 | 4.07 |
| CPT + 6 | 8 | IP | 6/100 | 11.8 ± 0.9 | 1.6 | 10.7 | 3.72 |

*This group has 4 of 8 tumors < 4× at Day 22.
Abbreviations: CDDP (cis-platin) and CPT (compothecin) and IP (intraperitoneal injection).

This data illustrates the efficacy of the imidazolines in the chemopotentiation of commonly used anticancer drugs. Inhibition of chemoresistance by these novel NF-κB inhibitors (especially compound 4) results in a significant delay of tumor growth as compared to treatment of the tumors with the anticancer drug alone.

In pharmaceutical compositions, the imidazoline is inhibitory at a dosage of 1 to 1,000 micrograms per milliliter or gram. It can be used in a ratio of 1 to 100 or 100 to 1 with the antitumor compound. In a preferred embodiment, one or more of the imidazolines for treating a patient are provided to the patient at an inhibitory dose in a pharmaceutically acceptable carrier. As such, the imidazolines are processed with pharmaceutical carrier substances by methods well known in the art such as by means of conventional mixing, granulating, coating, suspending and encapsulating methods, into the customary preparations for oral or rectal administration. Thus, imidazoline preparations for oral application can be obtained by combining one or more of the anthraquinones with solid pharmaceutical carriers; optionally granulating the resulting mixture; and processing the mixture or granulate, if desired and/or optionally after the addition of suitable auxiliaries, into the form of tablets or dragee cores.

Suitable pharmaceutical carriers for solid preparations are, in particular, fillers such as sugar, for example, lactose, saccharose, mannitol or sorbitol, cellulose preparations and/or calcium phosphates, for example, tricalcium phosphate or calcium hydrogen phosphate; also binding agents, such as starch paste, with the use, for example, of maize, wheat, rice or potato starch, gelatine, tragacanth, methyl cellulose, hydroxypropylmethyl cellulose, sodium carboxymethyl cellulose and/or polyvinylpyrrolidone, esters of polyacrylates or polymethacrylates with partially free functional groups; and/or, if required, effervescent agents, such as the abovementioned starches, also carboxymethyl starch, cross-linked polyvinylpyrrolidone, agar, or alginic acid or a salt thereof, such as sodium alginate. Auxiliaries are primarily flow-regulating agents and lubricating agents, for example, silicic acid, talcum, stearic acid or salts thereof, such as magnesium stearate or calcium stearate. Dragee cores are provided with suitable coatings, optionally resistant to gastric juices, whereby there are used, inter alia, concentrated sugar solutions optionally containing gum arabic, talcum, polyvinylpyrrolidone, and/or titanium dioxide, lacquer solutions in aqueous solvents or, for producing coatings resistant to stomach juices, solutions of esters of polyacrylates or polymethacrylates having partially free functional groups, or of suitable cellulose preparations such as acetylcellulose phthalate or hydroxypropyl-methylcellulose phthalate, with or without suitable softeners such as phthalic acid ester or triacetin. Dyestuffs or pigments may be added to the tablets or dragee coatings, for example for identification or marking of the various doses of active ingredient.

Imidazoline preparations comprising one or more of the anthraquinones which can be administered orally further include hard gelatine capsules, as well as hard or soft closed capsules made from gelatine and, if required, a softener such as glycerin or sorbitol. The hard gelatine capsules can contain one or more of the imidazolines in the form of a granulate, for example in admixture with fillers such as maize starch, optionally granulated wheat starch, binders or lubricants such as talcum, magnesium stearate or colloidal silicic acid, and optionally stabilizers. In closed capsules, the one or more of the imidazolines is in the form of a powder or granulate; or it is preferably present in the form of a suspension in suitable solvent, whereby for stabilizing the suspensions there can be added, for example, glycerin monostearate.

Other imidazoline preparations to be administered orally are, for example, aqueous suspensions prepared in the usual manner, which suspensions contain the one or more of the anthraquinones in the suspended form and at a concentration rendering a single dose sufficient. The aqueous suspensions either contain at most small amounts of stabilizers and/or flavoring substances, for example, sweetening agents such as saccharin-sodium, or as syrups contain a certain amount of sugar and/or sorbitol or similar substances. Also suitable are, for example, concentrates or concentrated suspensions for the preparation of shakes. Such concentrates can also be packed in single-dose amounts.

Suitable imidazoline preparations for rectal administration are, for example, suppositories consisting of a mixture of one or more of the imidazolines with a suppository foundation substance. Such substances are, in particular, natural or synthetic triglyceride mixtures. Also suitable are gelatine rectal capsules consisting of a suspension of the one or more of the imidazolines in a foundation substance. Suitable foundation substances are, for example, liquid triglycerides, of higher or, in particular, medium saturated fatty acids.

Likewise of particular interest are preparations containing the finely ground one or more of the imidazolines, preferably that having a median of particle size of 5 $\mu$m or less, in admixture with a starch, especially with maize starch or wheat starch, also, for example, with potato starch or rice starch. They are produced preferably by means of a brief mixing in a high-speed mixer having a propeller-like, sharp-edged stirring device, for example with a mixing time of between 3 and 10 minutes, and in the case of larger amounts of constituents with cooling if necessary. In this mixing process, the particles of the one or more of the imidazolines are uniformly deposited, with a continuing reduction of the size of some particles, onto the starch particles. The mixtures mentioned can be processed with the customary, for example, the aforementioned, auxiliaries into the form of solid dosage units; i.e., pressed for example into the form of tablets or dragees or filled into capsules. They can however also be used directly, or after the addition of auxiliaries, for example, pharmaceutically acceptable wetting agents and distributing agents, such as esters of polyoxyethylene sorbitans with higher fatty acids or sodium lauryl sulphate, and/or flavoring substances, as concentrates for the preparation of aqueous suspensions, for example, with about 5- to 20-fold amount of water. Instead of combining the imidazoline/starch mixture with a surface-active substance or with other auxiliaries, these substances may also be added to the water used to prepare the suspension. The concentrates for producing suspensions, consisting of the one or more of the imidazoline/starch mixtures and optionally auxiliaries, can be packed in single-dose amounts, if required in an airtight and moisture-proof manner.

In addition, the one or more imidazolines can be administered to a patient intraperitoneally, intranasally, subcutaneously, or intravenously. In general, for intraperitoneal, intranasal, subcutaneous, or intravenous administration, one or more of the imidazolines are provided by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the one or more imidazolines are provided in a composition acceptable for intraperitoneal, subcutaneous, or intravenous use in warm-blooded animals or humans. For example, such compositions can comprise a physiologically acceptable solution such as a buffered phosphate salt solution as a carrier for the one or more anthraquinones. Preferably, the solution is at a physiological pH. In particular embodiments, the composition is injected directly into the patient perfused through the tumor by intravenous administration.

Preparations according to the present invention comprise one or more of the imidazolines at a concentration suitable for administration to warm-blooded animals or humans which concentration is, depending on the mode of administration, between about 0.3% and 95%, preferably between about 2.5% and 90%. In the case of suspensions, the concentration is usually not higher than 30%, preferably about 2.5%; and conversely in the case of tablets, dragees and capsules with the one or more of the anthraquinones, the concentration is preferably not lower than about 0.3%, in order to ensure an easy ingestion of the required doses of the one or more imidazolines. The treatment of patients with the preparations comprising one or more of the imidazolines is carried out preferably by one or more administrations of a dose of the one or more imidazoline which over time is sufficient to substantially inhibit NF-κB. If required, the doses can be administered daily or divided into several partial doses which are administered at intervals of several hours. In particular cases, the preparations can be used in conjunction with or following one or more other therapies such as radiation or chemotherapy. The administered dose of the one or more imidazolines is dependent both on the patient (species of warm-blooded animal or human) to be treated, the general condition of the patient to be treated, and on the type of disease to be treated.

It is intended that the foregoing description be only illustrative of the present invention and that the present invention be limited only by the hereinafter appended claims.

We claim:
1. An imidazoline of the formula:

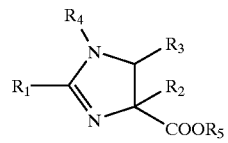

wherein $R_1$ is aryl, optionally substituted, $R_2$ is selected from the group consisting of alkyl, acyl, aryl, aralkyl, heteroaryl containing 5 to 14 ring members, and heterocyclic containing 5 to 12 ring members; $R_3$ is aryl, optionally substituted, $R_4$ is aralkyl, optionally substituted, and $R_5$ is selected from the group consisting of hydrogen and an alkyl group, all of which are optionally substituted.

2. The imidazoline of claim 1 wherein $R_1$ is phenyl.
3. The imidazoline of claim 1 wherein $R_4$ is benzyl.
4. The imidazoline of claim 1 wherein $R_5$ is lower alkyl containing 1 to 4 carbon atoms.
5. The imidazoline of claim 4 wherein $R_5$ is ethyl.
6. The imidazoline of claim 1 wherein $R_2$ is lower alkyl containing 1 to 4 carbon atoms.
7. The imidazoline of claim 6 wherein $R_2$ is methyl.
8. The imidazoline of claim 1 wherein $R_3$ is selected from the group consisting of phenyl and substituted phenyl.
9. The imidazoline of claim 1 wherein (Compound 1) $R_1$ is phenyl, $R_2$ is methyl, $R_3$ is phenyl, $R_4$ is benzyl and $R_5$ is H.
10. The imidazoline of claim 1 wherein (Compound 2) $R_1$ is phenyl, $R_2$ is methyl, $R_3$ is 4-methoxyphenyl, $R_4$ is benzyl and $R_5$ is H.
11. The imidazoline of claim 1 wherein (compound 4) wherein $R_1$ is phenyl, $R_2$ is phenyl, $R_3$ is phenyl, $R_4$ is benzyl and $R_5$ is H.
12. An imidazoline of formula:

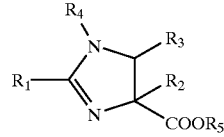

wherein (compound 5)
wherein $R_1$ is phenyl, $R_2$ is 1H-indol-3-ylmethyl, $R_3$ is phenyl, $R_4$ is benzyl and $R_5$ is H.
phenyl, $R_4$ is benzyl and $R_5$ is H.

13. The imidazoline of claim 1 wherein (Compound 10) $R_1$ is phenyl, $R_2$ is methyl, $R_3$ is phenyl, $R_4$ is benzyl and $R_5$ is ethyl.

14. A composition which comprises an imidazoline of the formula

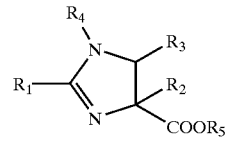

wherein $R_1$ is aryl, optionally substituted, $R_2$ is selected from the group consisting of alkyl, acyl, aryl, aralkyl, heteroaryl containing 5 to 14 ring members, and heterocyclic containing 5 to 12 ring members; $R_3$ is aryl, optionally substituted, $R_4$ is aralkyl, optionally substituted, and $R_5$ is selected from the group consisting of hydrogen and an alkyl group, all of which are optionally substituted; and (b) a drug which inhibits growth of a tumor or cancer.
15. The composition of claim 14 wherein the drug is a platinate.
16. The composition of claim 14 wherein the drug is camptothecin.
17. The composition of any one of claims 14, 15 or 16 further comprising a pharmaceutical carrier.
18. An imidazoline of the formula:

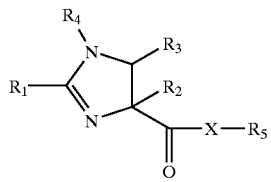

wherein $R_1$ is aryl, optionally substituted, $R_2$ is selected from the group consisting of alkyl, acyl, aryl, arylalkyl, heteroaryl containing 5 to 14 ring members, and heterocyclic containing 5 to 12 ring members; $R_3$ is aryl, optionally substituted, $R_4$ is aralkyl, optionally substituted; X is selected from the group consisting of O and S; and $R_5$ is selected from the group consisting of hydrogen, alkyl, acyl, aryl arylalkyl, heteroaryl, $NH_2$, NH—$R_6$ and

where $R_6$ and $R_7$ are selected from the group consisting of hydrogen, alkyl, aryl, arylalkyl, and heteroaryl and heterocyclic, which may be the same or different.

19. An imidazoline of the formula

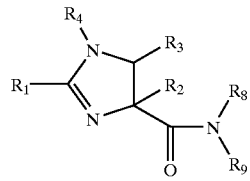

wherein $R_1$ is aryl, optionally substituted, $R_2$ is selected from the group consisting of alkyl, acyl, aryl, arylalkyl, heteroaryl containing 5 to 14 ring members, and heterocyclic containing 5 to 12 ring members; $R_3$ is aryl, optionally substituted, $R_4$ is aralkyl, optionally substituted, and wherein $R_8$ and $R_9$ and selected from the group consisting of hydrogen, alkyl, aryl, arylalkyl, heteroaryl and heterocyclic, which may be the same or different.

20. An imidazoline of the formula:

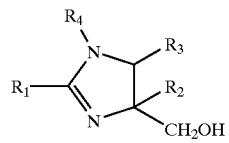

wherein $R_1$ is aryl, optionally substituted, $R_2$ is selected from the group consisting of alkyl, acyl, aryl, aralkyl, heteroaryl containing 5 to 14 ring members, and heterocyclic containing 5 to 12 ring members; $R_3$ is aryl, optionally substituted, $R_4$ is aralkyl, optionally substituted, and $R_5$ is selected from the group consisting of hydrogen and an alkyl group.

* * * * *

UNITED STATES PATENT AND TRADEMARK OFFICE
CERTIFICATE OF CORRECTION

PATENT NO. : 6,878,735 B2
DATED : April 12, 2005
INVENTOR(S) : Jetze J. Tepe and SatyamaheshwarPeddibhotla It is certified that error appears in the above-identified patent and that said Letters Patent is hereby corrected as shown below:

Column 12,
Line 58, "65-70%" should be -- 65-78% --.

Columns 13 and 14,
Scheme 2, "Me2Si" in the third and fourth structures should be -- Me3Si --.

Column 15,
Line 30, "rom temperature" should be -- room temperature --.
Line 32, "precipitated our as a" should be -- precipitated as a --.
Line 58, "762-7.68(1H" should be -- 7.62-7.68(1H --.

Column 19,
Line 51, "evaporoated" should be -- evaporated --.

Column 22,
Line 15, "614 g/mL" should be -- 614 g/mL --.

Column 24,
Line 49, "CPT (compothecin)" should be -- CPT (camtothecin) --.

Column 27,
Line 67, "phenyl, R4 is benzyl and R5 is H." should be deleted.

Signed and Sealed this

Nineteenth Day of July, 2005

JON W. DUDAS
*Director of the United States Patent and Trademark Office*